(12) United States Patent
Wagner et al.

(10) Patent No.: US 8,680,259 B2
(45) Date of Patent: Mar. 25, 2014

(54) METHOD AND COMPOSITIONS FOR THE IDENTIFICATION OF AGENTS THAT HAVE A POTENTIAL EFFECT AGAINST CHRONIC INFLAMMATORY DISEASES

(75) Inventors: Ulf Wagner, Leipzig (DE); Manuela Rossol, Leipzig (DE)

(73) Assignee: Universität Leipzig, Leipzig (DE)

( * ) Notice: Subject to any disclaimer, the term of this patent is extended or adjusted under 35 U.S.C. 154(b) by 0 days.

(21) Appl. No.: 13/813,179

(22) PCT Filed: Jul. 29, 2011

(86) PCT No.: PCT/EP2011/063139
§ 371 (c)(1),
(2), (4) Date: Mar. 17, 2013

(87) PCT Pub. No.: WO2012/013799
PCT Pub. Date: Feb. 2, 2012

(65) Prior Publication Data
US 2013/0211061 A1    Aug. 15, 2013

(30) Foreign Application Priority Data

Jul. 30, 2010  (EP) .................................. 10171469

(51) Int. Cl.
*C07H 21/04* (2006.01)
*A61K 38/00* (2006.01)

(52) U.S. Cl.
USPC ....................................... 536/24.5; 514/20.6

(58) Field of Classification Search
None
See application file for complete search history.

(56) References Cited

U.S. PATENT DOCUMENTS

| 6,916,956 | B2 | 7/2005 | Shinagawa et al. |
| 7,211,685 | B2 | 5/2007 | Shinagawa et al. |
| 2009/0142323 | A1* | 6/2009 | Quarles et al. ............... 424/94.1 |

FOREIGN PATENT DOCUMENTS

| WO | 98/34619 | A1 | 8/1998 |
| WO | 2008041118 | A2 | 4/2008 |
| WO | 2009001214 | A2 | 12/2008 |
| WO | 2009073544 | A2 | 6/2009 |

OTHER PUBLICATIONS

Pi et al, Impaired Osteoblast Function in GPRC6A Null Mice, published online Dec. 2009, Journal of Bone and Mineral Research, vol. 25, 5: 1092-1102.*
Harno E. et al: Evidence for the presence of GPRC6A receptors in rat mesenteric arteries; cell Calsium (2008) 44, 210-219; international search report.
Takahashi A. et al.: Measurement of Intracellular Calcium; Physiological Reviews; vol. 79; No. 4 (1999) pp. 1089-1125; specification; page 5, 4th paragraph.
Paredes M. et al.: Chemical Calcium Indicators; Methods, 2008, Nov. 46(3), pp. 143-151; specification; p. 5, 4th paragraph.
Rossol M. et al.: The contact-mediated response of peripheral-blood monocytes to preactivated T cells is suppressed by serum factors in rheumatoid arthritis; Arthritis Research & Therapy 2005, 7: R1189-R1199; specification; p. 11, 4th paragraph.
Rossol M. et al.: Interaction between transmembrane TNF and TNFR12/2 mediates the activation of monocytes by contact with T cells; The Journal of Immunology; 179; pp. 4239-4248; specification; p. 11, 4th paragraph; p. 12, last paragraph; p. 13, 3rd paragraph.
Wellendorph P. et al.: No evidence for a bone phenotype in GPRC6A knockout mice under normal physiological conditions; Journal of Molecular Endocrinology (2009) 42; 215-223; specification; p. 14, 1st paragraph.

* cited by examiner

*Primary Examiner* — Tracy Vivlemore
*Assistant Examiner* — Kate Poliakova-Georgan
(74) *Attorney, Agent, or Firm* — Gudrun E. Huckett

(57) ABSTRACT

The present invention is based on two important experimental observations: The first observation is that increased extracellular concentrations of ionized calcium are found in erosive arthritis and stimulate monocytic IL-1β release via the CaSR and GPRC6A. Simultaneous stimulation of monocytes with calcium ions and selected TLR ligands results in a 20-fold increased IL1β response compared to lipopolysaccharide (LPS) alone. During the crosstalk between GPCR and TLR signaling, phospholipase C is activated, which triggers calcium dependent potassium channels, resulting in potassium efflux, caspase-1 activation and IL-1β release. The amplification of IL1β secretion at sites of locally increased calcium ion concentrations aggravates rheumatoid arthritis. The second important observation is that both CaSR and GPRC6A, are highly expressed in the synovial membrane of patients with rheumatoid arthritis, but expression of GPRC6A, but not of CaSR, is lower in patients with osteoarthritis (s. FIG. 1). The latter is generally not accompanied by inflammation. Thus, expression of GPRC6A appears to be upregulated in chronic inflammatory situations. Based on these experimental observations the invention provides a method and compositions for the identification of agents that have a potential effect against chronic inflammatory conditions, in particular erosive arthritis and atherosclerosis.

4 Claims, 6 Drawing Sheets a b c

SEQUENCE LISTING

<160> NUMBER OF SEQ ID NOS: 12

<210> SEQ ID NO 1
<211> LENGTH: 97
<212> TYPE: DNA
<213> ORGANISM: Artificial
<220> FEATURE:
<223> OTHER INFORMATION: shRNA

<400> SEQUENCE: 1
tgctgttgac agtgagcgcg catattcaat cattctcaaa tagtgaagcc acagatgtat    60
ttgagaatga ttgaatatgc atgcctactg cctcgga    97

<210> SEQ ID NO 2
<211> LENGTH: 97
<212> TYPE: DNA
<213> ORGANISM: Artificial
<220> FEATURE:
<223> OTHER INFORMATION: shRNA

<400> SEQUENCE: 2
tgctgttgac agtgagcgac cagtgacttc catcaaatta tagtgaagcc acagatgtat    60
aatttgatgg aagtcactgg gtgcctactg cctcgga    97

<210> SEQ ID NO 3
<211> LENGTH: 97
<212> TYPE: DNA
<213> ORGANISM: Artificial
<220> FEATURE:
<223> OTHER INFORMATION: shRNA

<400> SEQUENCE: 3
tgctgttgac agtgagcgac cttcagcttt gatcccaaat tagtgaagcc acagatgtaa    60
tttgggatca aagctgaagg ctgcctactg cctcgga    97

<210> SEQ ID NO 4
<211> LENGTH: 57
<212> TYPE: DNA
<213> ORGANISM: Artificial
<220> FEATURE:
<223> OTHER INFORMATION: shRNA

<400> SEQUENCE: 4
ccggcgatcc ttattatctt cacttctcga gaagtgaaga taataaggat cgttttt    57

<210> SEQ ID NO 5

-continued

```
<211> LENGTH: 57
<212> TYPE: DNA
<213> ORGANISM: Artificial
<220> FEATURE:
<223> OTHER INFORMATION: shRNA

<400> SEQUENCE: 5
ccggccagga ctcattcata gtattctcga gaatactatg aatgagtcct ggttttt        57

<210> SEQ ID NO 6
<211> LENGTH: 57
<212> TYPE: DNA
<213> ORGANISM: Artificial
<220> FEATURE:
<223> OTHER INFORMATION: shRNA

<400> SEQUENCE: 6
ccgggctgtg gagattattg tcatactcga gtatgacaat aatctccaca gcttttt        57

<210> SEQ ID NO 7
<211> LENGTH: 57
<212> TYPE: DNA
<213> ORGANISM: Artificial
<220> FEATURE:
<223> OTHER INFORMATION: shRNA

<400> SEQUENCE: 7
ccggccacaa atccaggagt gtgttctcga gaacacactc ctggatttgt ggttttt        57

<210> SEQ ID NO 8
<211> LENGTH: 57
<212> TYPE: DNA
<213> ORGANISM: Artificial
<220> FEATURE:
<223> OTHER INFORMATION: shRNA

<400> SEQUENCE: 8
ccgggaagca aataacgtgt gcatactcga gtatgcacac gttatttgct tctttt         57

<210> SEQ ID NO 9
<211> LENGTH: 2860
<212> TYPE: DNA
<213> ORGANISM: homo sapiens
<220> FEATURE:
<221> NAME/KEY: CDS
<222> LOCATION: (23)..(2803)

<400> SEQUENCE: 9
actgagcaaa tgagatagaa ac atg gca ttc tta att ata cta att acc tgc       52
                         Met Ala Phe Leu Ile Ile Leu Ile Thr Cys
                          1               5                  10 ttt gtg att att ctt gct act tca cag cct tgc cag acc cct gat gac      100
Phe Val Ile Ile Leu Ala Thr Ser Gln Pro Cys Gln Thr Pro Asp Asp
             15                  20                  25 ttt gtg gct gcc act tct ccg gga cat atc ata att gga ggt ttg ttt      148
Phe Val Ala Ala Thr Ser Pro Gly His Ile Ile Ile Gly Gly Leu Phe
         30                  35                  40 gct att cat gaa aaa atg ttg tcc tca gaa gac tct ccc aga cga cca      196
Ala Ile His Glu Lys Met Leu Ser Ser Glu Asp Ser Pro Arg Arg Pro
     45                  50                  55 caa atc cag gag tgt gtt ggc ttt gaa ata tca gtt ttt ctt caa act      244
Gln Ile Gln Glu Cys Val Gly Phe Glu Ile Ser Val Phe Leu Gln Thr
 60                  65                  70 ctt gcc atg ata cac agc att gag atg atc aac aat tca aca ctc tta      292
Leu Ala Met Ile His Ser Ile Glu Met Ile Asn Asn Ser Thr Leu Leu
75                  80                  85                  90
```

```
cct gga gtc aaa ctg ggg tat gaa atc tat gac act tgt aca gaa gtc      340
Pro Gly Val Lys Leu Gly Tyr Glu Ile Tyr Asp Thr Cys Thr Glu Val
            95                  100                 105 aca gtg gca atg gca gcc act ctg agg ttt ctt tct aaa ttc aac tgc      388
Thr Val Ala Met Ala Ala Thr Leu Arg Phe Leu Ser Lys Phe Asn Cys
            110                 115                 120 tcc aga gaa act gtg gag ttt aag tgt gac tat tcc agc tac atg cca      436
Ser Arg Glu Thr Val Glu Phe Lys Cys Asp Tyr Ser Ser Tyr Met Pro
            125                 130                 135 aga gtt aag gct gtc ata ggt tct ggg tac tca gaa ata act atg gct      484
Arg Val Lys Ala Val Ile Gly Ser Gly Tyr Ser Glu Ile Thr Met Ala
            140                 145                 150 gtc tcc agg atg ttg aat tta cag ctc atg cca cag gtg ggt tat gaa      532
Val Ser Arg Met Leu Asn Leu Gln Leu Met Pro Gln Val Gly Tyr Glu
155                 160                 165                 170 tca act gca gaa atc ctg agt gac aaa att cgc ttt cct tca ttt tta      580
Ser Thr Ala Glu Ile Leu Ser Asp Lys Ile Arg Phe Pro Ser Phe Leu
                175                 180                 185 cgg act gtg ccc agt gac ttc cat caa att aaa gca atg gct cac ctg      628
Arg Thr Val Pro Ser Asp Phe His Gln Ile Lys Ala Met Ala His Leu
                190                 195                 200 att cag aaa tct ggt tgg aac tgg att ggc atc ata acc aca gat gat      676
Ile Gln Lys Ser Gly Trp Asn Trp Ile Gly Ile Ile Thr Thr Asp Asp
                205                 210                 215 gac tat gga cga ttg gct ctt aac act ttt ata att cag gct gaa gca      724
Asp Tyr Gly Arg Leu Ala Leu Asn Thr Phe Ile Ile Gln Ala Glu Ala
220                 225                 230 aat aac gtg tgc ata gcc ttc aaa gag gtt ctt cca gcc ttt ctt tca      772
Asn Asn Val Cys Ile Ala Phe Lys Glu Val Leu Pro Ala Phe Leu Ser
235                 240                 245                 250 gat aat acc att gaa gtc aga atc aat cgg aca ctg aag aaa atc att      820
Asp Asn Thr Ile Glu Val Arg Ile Asn Arg Thr Leu Lys Lys Ile Ile
                255                 260                 265 tta gaa gcc cag gtt aat gtc att gtg gta ttt ctg agg caa ttc cat      868
Leu Glu Ala Gln Val Asn Val Ile Val Val Phe Leu Arg Gln Phe His
                270                 275                 280 gtt ttt gat ctc ttc aat aaa gcc att gaa atg aat ata aat aag atg      916
Val Phe Asp Leu Phe Asn Lys Ala Ile Glu Met Asn Ile Asn Lys Met
                285                 290                 295 tgg att gct agt gat aat tgg tca act gcc acc aag att acc acc att      964
Trp Ile Ala Ser Asp Asn Trp Ser Thr Ala Thr Lys Ile Thr Thr Ile
300                 305                 310 cct aat gtt aaa aag att ggc aaa gtt gta ggg ttt gcc ttt aga aga     1012
Pro Asn Val Lys Lys Ile Gly Lys Val Val Gly Phe Ala Phe Arg Arg
315                 320                 325                 330 ggg aat ata tcc tct ttc cat tcc ttt ctt caa aat ctg cac ttg ctt     1060
Gly Asn Ile Ser Ser Phe His Ser Phe Leu Gln Asn Leu His Leu Leu
                335                 340                 345 ccc agt gac agt cac aaa ctc tta cat gaa tat gcc atg cat tta tct     1108
Pro Ser Asp Ser His Lys Leu Leu His Glu Tyr Ala Met His Leu Ser
                350                 355                 360 gcc tgc gca tat gtc aag gac act gat ttg agt caa tgc ata ttc aat     1156
Ala Cys Ala Tyr Val Lys Asp Thr Asp Leu Ser Gln Cys Ile Phe Asn
                365                 370                 375 cat tct caa agg act ttg gcc tac aag gct aac aag gct ata gaa agg     1204
His Ser Gln Arg Thr Leu Ala Tyr Lys Ala Asn Lys Ala Ile Glu Arg
                380                 385                 390 aac ttc gtc atg aga aat gac ttc ctc tgg gac tat gct gag cca gga     1252
Asn Phe Val Met Arg Asn Asp Phe Leu Trp Asp Tyr Ala Glu Pro Gly
395                 400                 405                 410
```

```
ctc att cat agt att cag ctt gca gtg ttt gcc ctt ggt tat gcc att    1300
Leu Ile His Ser Ile Gln Leu Ala Val Phe Ala Leu Gly Tyr Ala Ile
            415                 420                 425 cgg gat ctg tgt caa gct cgt gac tgt cag aac ccc aac gcc ttt caa    1348
Arg Asp Leu Cys Gln Ala Arg Asp Cys Gln Asn Pro Asn Ala Phe Gln
                430                 435                 440 cca tgg gag tta ctt ggt gtg cta aaa aat gtg aca ttc act gat gga    1396
Pro Trp Glu Leu Leu Gly Val Leu Lys Asn Val Thr Phe Thr Asp Gly
            445                 450                 455 tgg aat tca ttt cat ttt gat gct cac ggg gat tta aat act gga tat    1444
Trp Asn Ser Phe His Phe Asp Ala His Gly Asp Leu Asn Thr Gly Tyr
        460                 465                 470 gat gtt gtg ctc tgg aag gag atc aat gga cac atg act gtc act aag    1492
Asp Val Val Leu Trp Lys Glu Ile Asn Gly His Met Thr Val Thr Lys
475                 480                 485                 490 atg gca gaa tat gac cta cag aat gat gtc ttc atc atc cca gat cag    1540
Met Ala Glu Tyr Asp Leu Gln Asn Asp Val Phe Ile Ile Pro Asp Gln
                495                 500                 505 gaa aca aaa aat gag ttc agg aat ctt aag caa att caa tct aaa tgc    1588
Glu Thr Lys Asn Glu Phe Arg Asn Leu Lys Gln Ile Gln Ser Lys Cys
            510                 515                 520 tcc aag gaa tgc agt cct ggg caa atg aag aaa act aca aga agt caa    1636
Ser Lys Glu Cys Ser Pro Gly Gln Met Lys Lys Thr Thr Arg Ser Gln
        525                 530                 535 cac atc tgt tgc tat gaa tgt cag aac tgt cct gaa aat cat tac act    1684
His Ile Cys Cys Tyr Glu Cys Gln Asn Cys Pro Glu Asn His Tyr Thr
    540                 545                 550 aat cag aca gat atg cct cac tgc ctt tta tgc aac aac aaa act cac    1732
Asn Gln Thr Asp Met Pro His Cys Leu Leu Cys Asn Asn Lys Thr His
555                 560                 565                 570 tgg gcc cct gtt agg agc act atg tgc ttt gaa aag gaa gtg gaa tat    1780
Trp Ala Pro Val Arg Ser Thr Met Cys Phe Glu Lys Glu Val Glu Tyr
                575                 580                 585 ctc aac tgg aat gac tcc ttg gcc atc cta ctc ctg att ctc tcc cta    1828
Leu Asn Trp Asn Asp Ser Leu Ala Ile Leu Leu Leu Ile Leu Ser Leu
            590                 595                 600 ctg gga atc ata ttt gtt ctg gtt gtt ggc ata ata ttt aca aga aac    1876
Leu Gly Ile Ile Phe Val Leu Val Val Gly Ile Ile Phe Thr Arg Asn
        605                 610                 615 ctg aac aca cct gtt gtg aaa tca tcc ggg gga tta aga gtc tgc tat    1924
Leu Asn Thr Pro Val Val Lys Ser Ser Gly Gly Leu Arg Val Cys Tyr
    620                 625                 630 gtg atc ctt ctc tgt cat ttc ctc aat ttt gcc agc acg agc ttt ttc    1972
Val Ile Leu Leu Cys His Phe Leu Asn Phe Ala Ser Thr Ser Phe Phe
635                 640                 645                 650 att gga gaa cca caa gac ttc aca tgt aaa acc agg cag aca atg ttt    2020
Ile Gly Glu Pro Gln Asp Phe Thr Cys Lys Thr Arg Gln Thr Met Phe
                655                 660                 665 gga gtg agc ttt act ctt tgc atc tcc tgc att ttg acg aag tct ctg    2068
Gly Val Ser Phe Thr Leu Cys Ile Ser Cys Ile Leu Thr Lys Ser Leu
            670                 675                 680 aaa att ttg cta gcc ttc agc ttt gat ccc aaa tta cag aaa ttt ctg    2116
Lys Ile Leu Leu Ala Phe Ser Phe Asp Pro Lys Leu Gln Lys Phe Leu
        685                 690                 695 aag tgc ctc tat aga ccg atc ctt att atc ttc act tgc acg ggc atc    2164
Lys Cys Leu Tyr Arg Pro Ile Leu Ile Ile Phe Thr Cys Thr Gly Ile
    700                 705                 710 cag gtt gtc att tgc aca ctc tgg cta atc ttt gca gca cct act gta    2212
Gln Val Val Ile Cys Thr Leu Trp Leu Ile Phe Ala Ala Pro Thr Val
715                 720                 725                 730
```

-continued

```
gag gtg aat gtc tcc ttg ccc aga gtc atc atc ctg gag tgt gag gag    2260
Glu Val Asn Val Ser Leu Pro Arg Val Ile Ile Leu Glu Cys Glu Glu
            735                 740                 745 gga tcc ata ctt gca ttt ggc acc atg ctg ggc tac att gcc atc ctg    2308
Gly Ser Ile Leu Ala Phe Gly Thr Met Leu Gly Tyr Ile Ala Ile Leu
        750                 755                 760 gcc ttc att tgc ttc ata ttt gct ttc aaa ggc aaa tat gag aat tac    2356
Ala Phe Ile Cys Phe Ile Phe Ala Phe Lys Gly Lys Tyr Glu Asn Tyr
    765                 770                 775 aat gaa gcc aaa ttc att aca ttt ggc atg ctc att tac ttc ata gct    2404
Asn Glu Ala Lys Phe Ile Thr Phe Gly Met Leu Ile Tyr Phe Ile Ala
780                 785                 790 tgg atc aca ttc atc cct atc tat gct acc aca ttt ggc aaa tat gta    2452
Trp Ile Thr Phe Ile Pro Ile Tyr Ala Thr Thr Phe Gly Lys Tyr Val
795                 800                 805                 810 cca gct gtg gag att att gtc ata tta ata tct aac tat gga atc ctg    2500
Pro Ala Val Glu Ile Ile Val Ile Leu Ile Ser Asn Tyr Gly Ile Leu
                815                 820                 825 tat tgc aca ttc atc ccc aaa tgc tat gtt att att tgt aag caa gag    2548
Tyr Cys Thr Phe Ile Pro Lys Cys Tyr Val Ile Ile Cys Lys Gln Glu
            830                 835                 840 att aac aca aag tct gcc ttt ctc aag atg atc tac agt tat tct tcc    2596
Ile Asn Thr Lys Ser Ala Phe Leu Lys Met Ile Tyr Ser Tyr Ser Ser
        845                 850                 855 cat agt gtg agc agc att gcc ctg agt cct gct tca ctg gac tcc atg    2644
His Ser Val Ser Ser Ile Ala Leu Ser Pro Ala Ser Leu Asp Ser Met
    860                 865                 870 agc ggc aat gtc aca atg acc aat ccc agc tct agt ggc aag tct gca    2692
Ser Gly Asn Val Thr Met Thr Asn Pro Ser Ser Ser Gly Lys Ser Ala
875                 880                 885                 890 acc tgg cag aaa agc aaa gat ctt cag gca caa gca ttt gca cac ata    2740
Thr Trp Gln Lys Ser Lys Asp Leu Gln Ala Gln Ala Phe Ala His Ile
                895                 900                 905 tgc agg gaa aat gcc aca agt gta tct aaa act ttg cct cga aaa aga    2788
Cys Arg Glu Asn Ala Thr Ser Val Ser Lys Thr Leu Pro Arg Lys Arg
            910                 915                 920 atg tca agt ata tga ataagcctta ggagatgcca cattccagaa taaaatgttt    2843
Met Ser Ser Ile
        925 ccagggtctt tgcatct                                                 2860

<210> SEQ ID NO 10
<211> LENGTH: 926
<212> TYPE: PRT
<213> ORGANISM: homo sapiens

<400> SEQUENCE: 10

Met Ala Phe Leu Ile Ile Leu Ile Thr Cys Phe Val Ile Ile Leu Ala
1               5                   10                  15

Thr Ser Gln Pro Cys Gln Thr Pro Asp Asp Phe Val Ala Ala Thr Ser
            20                  25                  30

Pro Gly His Ile Ile Ile Gly Gly Leu Phe Ala Ile His Glu Lys Met
        35                  40                  45

Leu Ser Ser Glu Asp Ser Pro Arg Arg Pro Gln Ile Gln Glu Cys Val
    50                  55                  60

Gly Phe Glu Ile Ser Val Phe Leu Gln Thr Leu Ala Met Ile His Ser
65                  70                  75                  80

Ile Glu Met Ile Asn Asn Ser Thr Leu Leu Pro Gly Val Lys Leu Gly
            85                  90                  95
```

```
Tyr Glu Ile Tyr Asp Thr Cys Thr Glu Val Thr Val Ala Met Ala Ala
            100                 105                 110
Thr Leu Arg Phe Leu Ser Lys Phe Asn Cys Ser Arg Glu Thr Val Glu
            115                 120                 125
Phe Lys Cys Asp Tyr Ser Ser Tyr Met Pro Arg Val Lys Ala Val Ile
        130                 135                 140
Gly Ser Gly Tyr Ser Glu Ile Thr Met Ala Val Ser Arg Met Leu Asn
145                 150                 155                 160
Leu Gln Leu Met Pro Gln Val Gly Tyr Glu Ser Thr Ala Glu Ile Leu
                165                 170                 175
Ser Asp Lys Ile Arg Phe Pro Ser Phe Leu Arg Thr Val Pro Ser Asp
            180                 185                 190
Phe His Gln Ile Lys Ala Met Ala His Leu Ile Gln Lys Ser Gly Trp
        195                 200                 205
Asn Trp Ile Gly Ile Ile Thr Thr Asp Asp Asp Tyr Gly Arg Leu Ala
    210                 215                 220
Leu Asn Thr Phe Ile Ile Gln Ala Glu Ala Asn Asn Val Cys Ile Ala
225                 230                 235                 240
Phe Lys Glu Val Leu Pro Ala Phe Leu Ser Asp Asn Thr Ile Glu Val
                245                 250                 255
Arg Ile Asn Arg Thr Leu Lys Lys Ile Ile Leu Glu Ala Gln Val Asn
            260                 265                 270
Val Ile Val Val Phe Leu Arg Gln Phe His Val Phe Asp Leu Phe Asn
        275                 280                 285
Lys Ala Ile Glu Met Asn Ile Asn Lys Met Trp Ile Ala Ser Asp Asn
    290                 295                 300
Trp Ser Thr Ala Thr Lys Ile Thr Thr Ile Pro Asn Val Lys Lys Ile
305                 310                 315                 320
Gly Lys Val Val Gly Phe Ala Phe Arg Arg Gly Asn Ile Ser Ser Phe
                325                 330                 335
His Ser Phe Leu Gln Asn Leu His Leu Leu Pro Ser Asp Ser His Lys
            340                 345                 350
Leu Leu His Glu Tyr Ala Met His Leu Ser Ala Cys Ala Tyr Val Lys
        355                 360                 365
Asp Thr Asp Leu Ser Gln Cys Ile Phe Asn His Ser Gln Arg Thr Leu
    370                 375                 380
Ala Tyr Lys Ala Asn Lys Ala Ile Glu Arg Asn Phe Val Met Arg Asn
385                 390                 395                 400
Asp Phe Leu Trp Asp Tyr Ala Glu Pro Gly Leu Ile His Ser Ile Gln
                405                 410                 415
Leu Ala Val Phe Ala Leu Gly Tyr Ala Ile Arg Asp Leu Cys Gln Ala
            420                 425                 430
Arg Asp Cys Gln Asn Pro Asn Ala Phe Gln Pro Trp Glu Leu Leu Gly
        435                 440                 445
Val Leu Lys Asn Val Thr Phe Thr Asp Gly Trp Asn Ser Phe His Phe
    450                 455                 460
Asp Ala His Gly Asp Leu Asn Thr Gly Tyr Asp Val Val Leu Trp Lys
465                 470                 475                 480
Glu Ile Asn Gly His Met Thr Val Thr Lys Met Ala Glu Tyr Asp Leu
                485                 490                 495
Gln Asn Asp Val Phe Ile Ile Pro Asp Gln Glu Thr Lys Asn Glu Phe
            500                 505                 510
Arg Asn Leu Lys Gln Ile Gln Ser Lys Cys Ser Lys Glu Cys Ser Pro
```

```
                515                 520                 525
Gly Gln Met Lys Lys Thr Thr Arg Ser Gln His Ile Cys Cys Tyr Glu
        530                 535                 540

Cys Gln Asn Cys Pro Glu Asn His Tyr Thr Asn Gln Thr Asp Met Pro
545                 550                 555                 560

His Cys Leu Leu Cys Asn Asn Lys Thr His Trp Ala Pro Val Arg Ser
                565                 570                 575

Thr Met Cys Phe Glu Lys Glu Val Glu Tyr Leu Asn Trp Asn Asp Ser
            580                 585                 590

Leu Ala Ile Leu Leu Leu Ile Leu Ser Leu Leu Gly Ile Ile Phe Val
        595                 600                 605

Leu Val Val Gly Ile Ile Phe Thr Arg Asn Leu Asn Thr Pro Val Val
    610                 615                 620

Lys Ser Ser Gly Gly Leu Arg Val Cys Tyr Val Ile Leu Leu Cys His
625                 630                 635                 640

Phe Leu Asn Phe Ala Ser Thr Ser Phe Ile Gly Glu Pro Gln Asp
                645                 650                 655

Phe Thr Cys Lys Thr Arg Gln Thr Met Phe Gly Val Ser Phe Thr Leu
            660                 665                 670

Cys Ile Ser Cys Ile Leu Thr Lys Ser Leu Lys Ile Leu Leu Ala Phe
        675                 680                 685

Ser Phe Asp Pro Lys Leu Gln Lys Phe Leu Lys Cys Leu Tyr Arg Pro
    690                 695                 700

Ile Leu Ile Ile Phe Thr Cys Thr Gly Ile Gln Val Val Ile Cys Thr
705                 710                 715                 720

Leu Trp Leu Ile Phe Ala Ala Pro Thr Val Glu Val Asn Val Ser Leu
                725                 730                 735

Pro Arg Val Ile Ile Leu Glu Cys Glu Gly Ser Ile Leu Ala Phe
            740                 745                 750

Gly Thr Met Leu Gly Tyr Ile Ala Ile Leu Ala Phe Ile Cys Phe Ile
        755                 760                 765

Phe Ala Phe Lys Gly Lys Tyr Glu Asn Tyr Asn Glu Ala Lys Phe Ile
    770                 775                 780

Thr Phe Gly Met Leu Ile Tyr Phe Ile Ala Trp Ile Thr Phe Ile Pro
785                 790                 795                 800

Ile Tyr Ala Thr Thr Phe Gly Lys Tyr Val Pro Ala Val Glu Ile Ile
                805                 810                 815

Val Ile Leu Ile Ser Asn Tyr Gly Ile Leu Tyr Cys Thr Phe Ile Pro
            820                 825                 830

Lys Cys Tyr Val Ile Ile Cys Lys Gln Glu Ile Asn Thr Lys Ser Ala
        835                 840                 845

Phe Leu Lys Met Ile Tyr Ser Tyr Ser Ser His Ser Val Ser Ser Ile
    850                 855                 860

Ala Leu Ser Pro Ala Ser Leu Asp Ser Met Ser Gly Asn Val Thr Met
865                 870                 875                 880

Thr Asn Pro Ser Ser Ser Gly Lys Ser Ala Thr Trp Gln Lys Ser Lys
                885                 890                 895

Asp Leu Gln Ala Gln Ala Phe Ala His Ile Cys Arg Glu Asn Ala Thr
            900                 905                 910

Ser Val Ser Lys Thr Leu Pro Arg Lys Arg Met Ser Ser Ile
        915                 920                 925

<210> SEQ ID NO 11
<211> LENGTH: 5009
```

-continued

```
<212> TYPE: DNA
<213> ORGANISM: Homo sapiens
<220> FEATURE:
<221> NAME/KEY: CDS
<222> LOCATION: (439)..(3705)

<400> SEQUENCE: 11
ggggctgctg tggccggacc cgaaggcggg cgccgggagc gcagcgagcc agacgcgcct    60
ctccaagacc gtgaccttgg catagggagc ggggctgcgc gcagtcctga gatcagacca   120
gagctcatcc tcgtggagac ccacggccga ggggccggag ctgcctctgt gcgagggagc   180
cctggccgcg gcgcagaagg catcacagga ggcctctgca tgatgtggct tccaaagact   240
caaggaccac ccacattaca agtctggatt gaggaaggca gaaatggaga ttcaaacacc   300
acgtcttcta ttattttatt aatcaatctg tagacatgtg tccccactgc agggagtgaa   360
ctgctccaag ggagaaactt ctgggagcct ccaaactcct agctgtctca tcccttgccc   420
tggagagacg gcagaacc atg gca ttt tat agc tgc tgc tgg gtc ctc ttg    471
                    Met Ala Phe Tyr Ser Cys Cys Trp Val Leu Leu
                     1               5                  10 gca ctc acc tgg cac acc tct gcc tac ggg cca gac cag cga gcc caa    519
Ala Leu Thr Trp His Thr Ser Ala Tyr Gly Pro Asp Gln Arg Ala Gln
         15                  20                  25 aag aag ggg gac att atc ctt ggg ggg ctc ttt cct att cat ttt gga    567
Lys Lys Gly Asp Ile Ile Leu Gly Gly Leu Phe Pro Ile His Phe Gly
     30                  35                  40 gta gca gct aaa gat caa gat ctc aaa tca agg ccg gag tct gtg gaa    615
Val Ala Ala Lys Asp Gln Asp Leu Lys Ser Arg Pro Glu Ser Val Glu
 45                  50                  55 tgt atc agg tat aat ttc cgt ggg ttt cgc tgg tta cag gct atg ata    663
Cys Ile Arg Tyr Asn Phe Arg Gly Phe Arg Trp Leu Gln Ala Met Ile
 60                  65                  70                  75 ttt gcc ata gag gag ata aac agc agc cca gcc ctt ctt ccc aac ttg    711
Phe Ala Ile Glu Glu Ile Asn Ser Ser Pro Ala Leu Leu Pro Asn Leu
                 80                  85                  90 acg ctg gga tac agg ata ttt gac act tgc aac acc gtt tct aag gcc    759
Thr Leu Gly Tyr Arg Ile Phe Asp Thr Cys Asn Thr Val Ser Lys Ala
             95                 100                 105 ttg gaa gcc acc ctg agt ttt gtt gct caa aac aaa att gat tct ttg    807
Leu Glu Ala Thr Leu Ser Phe Val Ala Gln Asn Lys Ile Asp Ser Leu
         110                 115                 120 aac ctt gat gag ttc tgc aac tgc tca gag cac att ccc tct acg att    855
Asn Leu Asp Glu Phe Cys Asn Cys Ser Glu His Ile Pro Ser Thr Ile
     125                 130                 135 gct gtg gtg gga gca act ggc tca ggc gtc tcc acg gca gtg gca aat    903
Ala Val Val Gly Ala Thr Gly Ser Gly Val Ser Thr Ala Val Ala Asn
140                 145                 150                 155 ctg ctg ggg ctc ttc tac att ccc cag gtc agt tat gcc tcc tcc agc    951
Leu Leu Gly Leu Phe Tyr Ile Pro Gln Val Ser Tyr Ala Ser Ser Ser
                 160                 165                 170 aga ctc ctc agc aac aag aat caa ttc aag tct ttc ctc cga acc atc    999
Arg Leu Leu Ser Asn Lys Asn Gln Phe Lys Ser Phe Leu Arg Thr Ile
             175                 180                 185 ccc aat gat gag cac cag gcc act gcc atg gca gac atc atc gag tat   1047
Pro Asn Asp Glu His Gln Ala Thr Ala Met Ala Asp Ile Ile Glu Tyr
         190                 195                 200 ttc cgc tgg aac tgg gtg ggc aca att gca gct gat gac gac tat ggg   1095
Phe Arg Trp Asn Trp Val Gly Thr Ile Ala Ala Asp Asp Asp Tyr Gly
     205                 210                 215 cgg ccg ggg att gag aaa ttc cga gag gaa gct gag gaa agg gat atc   1143
Arg Pro Gly Ile Glu Lys Phe Arg Glu Glu Ala Glu Glu Arg Asp Ile
```

-continued

```
        220                 225                 230                 235 tgc atc gac ttc agt gaa ctc atc tcc cag tac tct gat gag gaa gag      1191
Cys Ile Asp Phe Ser Glu Leu Ile Ser Gln Tyr Ser Asp Glu Glu Glu
                        240                 245                 250 atc cag cat gtg gta gag gtg att caa aat tcc acg gcc aaa gtc atc      1239
Ile Gln His Val Val Glu Val Ile Gln Asn Ser Thr Ala Lys Val Ile
                    255                 260                 265 gtg gtt ttc tcc agt ggc cca gat ctt gag ccc ctc atc aag gag att      1287
Val Val Phe Ser Ser Gly Pro Asp Leu Glu Pro Leu Ile Lys Glu Ile
                270                 275                 280 gtc cgg cgc aat atc acg ggc aag atc tgg ctg gcc agc gag gcc tgg      1335
Val Arg Arg Asn Ile Thr Gly Lys Ile Trp Leu Ala Ser Glu Ala Trp
            285                 290                 295 gcc agc tcc tcc ctg atc gcc atg cct cag tac ttc cac gtg gtt ggc      1383
Ala Ser Ser Ser Leu Ile Ala Met Pro Gln Tyr Phe His Val Val Gly
300                 305                 310                 315 ggc acc att gga ttc gct ctg aag gct ggg cag atc cca ggc ttc cgg      1431
Gly Thr Ile Gly Phe Ala Leu Lys Ala Gly Gln Ile Pro Gly Phe Arg
                        320                 325                 330 gaa ttc ctg aag aag gtc cat ccc agg aag tct gtc cac aat ggt ttt      1479
Glu Phe Leu Lys Lys Val His Pro Arg Lys Ser Val His Asn Gly Phe
                    335                 340                 345 gcc aag gag ttt tgg gaa gaa aca ttt aac tgc cac ctc caa gaa ggt      1527
Ala Lys Glu Phe Trp Glu Glu Thr Phe Asn Cys His Leu Gln Glu Gly
                350                 355                 360 gca aaa gga cct tta cct gtg gac acc ttt ctg aga ggt cac gaa gaa      1575
Ala Lys Gly Pro Leu Pro Val Asp Thr Phe Leu Arg Gly His Glu Glu
            365                 370                 375 agt ggc gac agg ttt agc aac agc tcg aca gcc ttc cga ccc ctc tgt      1623
Ser Gly Asp Arg Phe Ser Asn Ser Ser Thr Ala Phe Arg Pro Leu Cys
380                 385                 390                 395 aca ggg gat gag aac atc agc agt gtc gag acc cct tac ata gat tac      1671
Thr Gly Asp Glu Asn Ile Ser Ser Val Glu Thr Pro Tyr Ile Asp Tyr
                        400                 405                 410 acg cat tta cgg ata tcc tac aat gtg tac tta gca gtc tac tcc att      1719
Thr His Leu Arg Ile Ser Tyr Asn Val Tyr Leu Ala Val Tyr Ser Ile
                    415                 420                 425 gcc cac gcc ttg caa gat ata tat acc tgc tta cct ggg aga ggg ctc      1767
Ala His Ala Leu Gln Asp Ile Tyr Thr Cys Leu Pro Gly Arg Gly Leu
                430                 435                 440 ttc acc aat ggc tcc tgt gca gac atc aag aaa gtt gag gcg tgg cag      1815
Phe Thr Asn Gly Ser Cys Ala Asp Ile Lys Lys Val Glu Ala Trp Gln
            445                 450                 455 gtc ctg aag cac cta cgg cat cta aac ttt aca aac aat atg ggg gag      1863
Val Leu Lys His Leu Arg His Leu Asn Phe Thr Asn Asn Met Gly Glu
460                 465                 470                 475 cag gtg acc ttt gat gag tgt ggt gac ctg gtg ggg aac tat tcc atc      1911
Gln Val Thr Phe Asp Glu Cys Gly Asp Leu Val Gly Asn Tyr Ser Ile
                        480                 485                 490 atc aac tgg cac ctc tcc cca gag gat ggc tcc atc gtg ttt aag gaa      1959
Ile Asn Trp His Leu Ser Pro Glu Asp Gly Ser Ile Val Phe Lys Glu
                    495                 500                 505 gtc ggg tat tac aac gtc tat gcc aag aag gga gaa aga ctc ttc atc      2007
Val Gly Tyr Tyr Asn Val Tyr Ala Lys Lys Gly Glu Arg Leu Phe Ile
                510                 515                 520 aac gag gag aaa atc ctg tgg agt ggg ttc tcc agg gag cca ctc acc      2055
Asn Glu Glu Lys Ile Leu Trp Ser Gly Phe Ser Arg Glu Pro Leu Thr
            525                 530                 535 ttt gtg ctg tct gtc ctc cag gtg ccc ttc tcc aac tgc agc cga gac      2103
Phe Val Leu Ser Val Leu Gln Val Pro Phe Ser Asn Cys Ser Arg Asp
```

-continued

```
                540                 545                 550                 555 tgc ctg gca ggg acc agg aaa ggg atc att gag ggg gag ccc acc tgc      2151
Cys Leu Ala Gly Thr Arg Lys Gly Ile Ile Glu Gly Glu Pro Thr Cys
                560                 565                 570 tgc ttt gag tgt gtg gag tgt cct gat ggg gag tat agt gat gag aca      2199
Cys Phe Glu Cys Val Glu Cys Pro Asp Gly Glu Tyr Ser Asp Glu Thr
                575                 580                 585 gat gcc agt gcc tgt aac aag tgc cca gat gac ttc tgg tcc aat gag      2247
Asp Ala Ser Ala Cys Asn Lys Cys Pro Asp Asp Phe Trp Ser Asn Glu
                590                 595                 600 aac cac acc tcc tgc att gcc aag gag atc gag ttt ctg tcg tgg acg      2295
Asn His Thr Ser Cys Ile Ala Lys Glu Ile Glu Phe Leu Ser Trp Thr
                605                 610                 615 gag ccc ttt ggg atc gca ctc acc ctc ttt gcc gtg ctg ggc att ttc      2343
Glu Pro Phe Gly Ile Ala Leu Thr Leu Phe Ala Val Leu Gly Ile Phe
620                 625                 630                 635 ctg aca gcc ttt gtg ctg ggt gtg ttt atc aag ttc cgc aac aca ccc      2391
Leu Thr Ala Phe Val Leu Gly Val Phe Ile Lys Phe Arg Asn Thr Pro
                640                 645                 650 att gtc aag gcc acc aac cga gag ctc tcc tac ctc ctc ctc ttc tcc      2439
Ile Val Lys Ala Thr Asn Arg Glu Leu Ser Tyr Leu Leu Leu Phe Ser
                655                 660                 665 ctg ctc tgc tgc ttc tcc agc tcc ctg ttc ttc atc ggg gag ccc cag      2487
Leu Leu Cys Cys Phe Ser Ser Ser Leu Phe Phe Ile Gly Glu Pro Gln
                670                 675                 680 gac tgg acg tgc cgc ctg cgc cag ccg gcc ttt ggc atc agc ttc gtg      2535
Asp Trp Thr Cys Arg Leu Arg Gln Pro Ala Phe Gly Ile Ser Phe Val
                685                 690                 695 ctc tgc atc tca tgc atc ctg gtg aaa acc aac cgt gtc ctc ctg gtg      2583
Leu Cys Ile Ser Cys Ile Leu Val Lys Thr Asn Arg Val Leu Leu Val
700                 705                 710                 715 ttt gag gcc aag atc ccc acc agc ttc cac cgc aag tgg tgg ggg ctc      2631
Phe Glu Ala Lys Ile Pro Thr Ser Phe His Arg Lys Trp Trp Gly Leu
                720                 725                 730 aac ctg cag ttc ctg ctg gtt ttc ctc tgc acc ttc atg cag att gtc      2679
Asn Leu Gln Phe Leu Leu Val Phe Leu Cys Thr Phe Met Gln Ile Val
                735                 740                 745 atc tgt gtg atc tgg ctc tac acc gcg ccc ccc tca agc tac cgc aac      2727
Ile Cys Val Ile Trp Leu Tyr Thr Ala Pro Pro Ser Ser Tyr Arg Asn
                750                 755                 760 cag gag ctg gag gat gag atc atc ttc atc acg tgc cac gag ggc tcc      2775
Gln Glu Leu Glu Asp Glu Ile Ile Phe Ile Thr Cys His Glu Gly Ser
                765                 770                 775 ctc atg gcc ctg ggc ttc ctg atc ggc tac acc tgc ctg ctg gct gcc      2823
Leu Met Ala Leu Gly Phe Leu Ile Gly Tyr Thr Cys Leu Leu Ala Ala
780                 785                 790                 795 atc tgc ttc ttc ttt gcc ttc aag tcc cgg aag ctg ccg gag aac ttc      2871
Ile Cys Phe Phe Phe Ala Phe Lys Ser Arg Lys Leu Pro Glu Asn Phe
                800                 805                 810 aat gaa gcc aag ttc atc acc ttc agc atg ctc atc ttc ttc atc gtc      2919
Asn Glu Ala Lys Phe Ile Thr Phe Ser Met Leu Ile Phe Phe Ile Val
                815                 820                 825 tgg atc tcc ttc att cca gcc tat gcc agc acc tat ggc aag ttt gtc      2967
Trp Ile Ser Phe Ile Pro Ala Tyr Ala Ser Thr Tyr Gly Lys Phe Val
                830                 835                 840 tct gcc gta gag gtg att gcc atc ctg gca gcc agc ttt ggc ttg ctg      3015
Ser Ala Val Glu Val Ile Ala Ile Leu Ala Ala Ser Phe Gly Leu Leu
                845                 850                 855 gcg tgc atc ttc ttc aac aag atc tac atc att ctc ttc aag cca tcc      3063
Ala Cys Ile Phe Phe Asn Lys Ile Tyr Ile Ile Leu Phe Lys Pro Ser
```

```
                860            865             870             875 cgc aac acc atc gag gag gtg cgt tgc agc acc gca gct cac gct ttc    3111
Arg Asn Thr Ile Glu Glu Val Arg Cys Ser Thr Ala Ala His Ala Phe
                    880                 885                 890 aag gtg gct gcc cgg gcc acg ctg cgc cgc agc aac gtc tcc cgc aag    3159
Lys Val Ala Ala Arg Ala Thr Leu Arg Arg Ser Asn Val Ser Arg Lys
            895                 900                 905 cgg tcc agc agc ctt gga ggc tcc acg gga tcc acc ccc tcc tcc tcc    3207
Arg Ser Ser Ser Leu Gly Gly Ser Thr Gly Ser Thr Pro Ser Ser Ser
        910                 915                 920 atc agc agc aag agc aac agc gaa gac cca ttc cca cgg ccc gag agg    3255
Ile Ser Ser Lys Ser Asn Ser Glu Asp Pro Phe Pro Arg Pro Glu Arg
    925                 930                 935 cag aag cag cag cag ccg ctg gcc cta acc cag caa gag cag cag cag    3303
Gln Lys Gln Gln Gln Pro Leu Ala Leu Thr Gln Gln Glu Gln Gln Gln
940                 945                 950                 955 cag ccc ctg acc ctc cca cag cag caa cga tct cag cag cag ccc aga    3351
Gln Pro Leu Thr Leu Pro Gln Gln Gln Arg Ser Gln Gln Gln Pro Arg
                960                 965                 970 tgc aag cag aag gtc atc ttt ggc agc ggc acg gtc acc ttc tca ctg    3399
Cys Lys Gln Lys Val Ile Phe Gly Ser Gly Thr Val Thr Phe Ser Leu
            975                 980                 985 agc ttt gat gag cct cag aag aac gcc atg gcc cac agg aat tct acg    3447
Ser Phe Asp Glu Pro Gln Lys Asn Ala Met Ala His Arg Asn Ser Thr
        990                 995                 1000 cac cag aac tcc ctg gag gcc cag aaa agc agc gat acg ctg acc       3492
His Gln Asn Ser Leu Glu Ala Gln Lys Ser Ser Asp Thr Leu Thr
    1005                1010                1015 cga cac cag cca tta ctc ccg ctg cag tgc ggg gaa acg gac tta       3537
Arg His Gln Pro Leu Leu Pro Leu Gln Cys Gly Glu Thr Asp Leu
1020                1025                1030 gat ctg acc gtc cag gaa aca ggt ctg caa gga cct gtg ggt gga       3582
Asp Leu Thr Val Gln Glu Thr Gly Leu Gln Gly Pro Val Gly Gly
    1035                1040                1045 gac cag cgg cca gag gtg gag gac cct gaa gag ttg tcc cca gca       3627
Asp Gln Arg Pro Glu Val Glu Asp Pro Glu Glu Leu Ser Pro Ala
1050                1055                1060 ctt gta gtg tcc agt tca cag agc ttt gtc atc agt ggt gga ggc       3672
Leu Val Val Ser Ser Ser Gln Ser Phe Val Ile Ser Gly Gly Gly
    1065                1070                1075 agc act gtt aca gaa aac gta gtg aat tca taa aatggaagga            3715
Ser Thr Val Thr Glu Asn Val Val Asn Ser
1080                1085 gaagactggg ctagggagaa tgcagagagg tttcttgggg tcccagggat gaggaatcgc  3775
cccagactcc tttcctctga ggaagaaggg ataatagaca catcaaatgc ccgaattta  3835 gtcacaccat cttaaatgac agtgaattga cccatgttcc ctttaaaatt aaaaaaaga  3895 agagccttgt gtttctgtgg ttgcatttgt caaagcattg agatctccac ggtcagattt  3955
gctgttcacc cacatctaat gtctcttcct ctgttctatc ccacccaaca gctcagagat  4015
gaaactatgg ctttaaacta ccctccagag tgtgcagact gatgggacat caaatttgcc  4075
accactagag ctgagagtct gaaagacaga atgtcaccag tcctgcccaa tgccttgaca  4135
acagactgaa tttaaatgt tcacaacata aggagaatgt atctcctcct atttatgaaa  4195
accatatgat attttgtctc ctacctgctg ctgctattat gtaacatcca gaaggtttgc  4255 accccctccta taccatatgt ctggttctgt ccaggacatg atactgatgc catgtttaga  4315
ttccaggatc acaagaatca cctcaaattg ttaggaaggg actgcataaa ccaatgagct  4375
```

```
gtatctgtaa ttaatattcc tatatgtagc tttatcctta ggaaaatgct tctgttgtaa    4435
tagtccatgg acaatataaa ctgaaaaatg tcagtctggt ttatataagg cagtattatt    4495
gagctctatt tccccacccc actatcctca ctcccataag ctaagcctta tgtgagcccc    4555
ttcagggact caagggtcca gaagtccctc ccatctctac cccaaagaat tcctgaagcc    4615
agatccaccc tatccctgta cagagtaagt tctcaattat tggcctgcta atagctgcta    4675
gggtaggaaa gcgtggttcc aagaaagatc caccctcaaa tgtcggagct atgttccctc    4735
cagcagtggt attaatactg ccggtcaccc aggctctgga gccagagaga cagaccgggg    4795
ttcaagccat ggcttcgtca tttgcaagct gagtgactgt aggcagggaa ccttaacctc    4855
tctaagccac agcttcttca tctttaaaat aaggataata atcattcctt cccctcagag    4915
ctcttatgtg gattaaacga gataatgtat ataaagtact ttagcctggt acctagcaca    4975
caataagcat tcaataaata ttagttaata ttat                                5009
```

<210> SEQ ID NO 12
<211> LENGTH: 1088
<212> TYPE: PRT
<213> ORGANISM: Homo sapiens

<400> SEQUENCE: 12

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270
```

```
Gly Pro Asp Leu Glu Pro Leu Ile Lys Glu Ile Val Arg Arg Asn Ile
            275                 280                 285

Thr Gly Lys Ile Trp Leu Ala Ser Glu Ala Trp Ala Ser Ser Ser Leu
            290                 295                 300

Ile Ala Met Pro Gln Tyr Phe His Val Val Gly Thr Ile Gly Phe
305                 310                 315                 320

Ala Leu Lys Ala Gly Gln Ile Pro Gly Phe Arg Glu Phe Leu Lys Lys
                    325                 330                 335

Val His Pro Arg Lys Ser Val His Asn Gly Phe Ala Lys Glu Phe Trp
                    340                 345                 350

Glu Glu Thr Phe Asn Cys His Leu Gln Gly Ala Lys Gly Pro Leu
            355                 360                 365

Pro Val Asp Thr Phe Leu Arg Gly His Glu Glu Ser Gly Asp Arg Phe
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                    405                 410                 415

Ser Tyr Asn Val Tyr Leu Ala Val Tyr Ser Ile Ala His Ala Leu Gln
                    420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                    485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Pro Leu Thr Phe Val Leu Ser Val
            530                 535                 540

Leu Gln Val Pro Phe Ser Asn Cys Ser Arg Asp Cys Leu Ala Gly Thr
545                 550                 555                 560

Arg Lys Gly Ile Ile Glu Gly Glu Pro Thr Cys Cys Phe Glu Cys Val
                    565                 570                 575

Glu Cys Pro Asp Gly Glu Tyr Ser Asp Glu Thr Asp Ala Ser Ala Cys
            580                 585                 590

Asn Lys Cys Pro Asp Asp Phe Trp Ser Asn Glu Asn His Thr Ser Cys
            595                 600                 605

Ile Ala Lys Glu Ile Glu Phe Leu Ser Trp Thr Glu Pro Phe Gly Ile
            610                 615                 620

Ala Leu Thr Leu Phe Ala Val Leu Gly Ile Phe Leu Thr Ala Phe Val
625                 630                 635                 640

Leu Gly Val Phe Ile Lys Phe Arg Asn Thr Pro Ile Val Lys Ala Thr
                    645                 650                 655

Asn Arg Glu Leu Ser Tyr Leu Leu Leu Phe Ser Leu Leu Cys Cys Phe
            660                 665                 670

Ser Ser Ser Leu Phe Phe Ile Gly Glu Pro Gln Asp Trp Thr Cys Arg
            675                 680                 685

Leu Arg Gln Pro Ala Phe Gly Ile Ser Phe Val Leu Cys Ile Ser Cys
```

-continued

```
            690                 695                 700
Ile Leu Val Lys Thr Asn Arg Val Leu Val Phe Glu Ala Lys Ile
705                 710                 715                 720

Pro Thr Ser Phe His Arg Lys Trp Trp Gly Leu Asn Leu Gln Phe Leu
                    725                 730                 735

Leu Val Phe Leu Cys Thr Phe Met Gln Ile Val Ile Cys Val Ile Trp
                    740                 745                 750

Leu Tyr Thr Ala Pro Pro Ser Ser Tyr Arg Asn Gln Glu Leu Glu Asp
                    755                 760                 765

Glu Ile Ile Phe Ile Thr Cys His Glu Gly Ser Leu Met Ala Leu Gly
        770                 775                 780

Phe Leu Ile Gly Tyr Thr Cys Leu Leu Ala Ala Ile Cys Phe Phe Phe
785                 790                 795                 800

Ala Phe Lys Ser Arg Lys Leu Pro Glu Asn Phe Asn Glu Ala Lys Phe
                    805                 810                 815

Ile Thr Phe Ser Met Leu Ile Phe Phe Ile Val Trp Ile Ser Phe Ile
                    820                 825                 830

Pro Ala Tyr Ala Ser Thr Tyr Gly Lys Phe Val Ser Ala Val Glu Val
                    835                 840                 845

Ile Ala Ile Leu Ala Ala Ser Phe Gly Leu Leu Ala Cys Ile Phe Phe
850                 855                 860

Asn Lys Ile Tyr Ile Ile Leu Phe Lys Pro Ser Arg Asn Thr Ile Glu
865                 870                 875                 880

Glu Val Arg Cys Ser Thr Ala Ala His Ala Phe Lys Val Ala Ala Arg
                    885                 890                 895

Ala Thr Leu Arg Arg Ser Asn Val Ser Arg Lys Arg Ser Ser Ser Leu
                    900                 905                 910

Gly Gly Ser Thr Gly Ser Thr Pro Ser Ser Ile Ser Ser Lys Ser
                    915                 920                 925

Asn Ser Glu Asp Pro Phe Pro Arg Pro Glu Arg Gln Lys Gln Gln
930                 935                 940

Pro Leu Ala Leu Thr Gln Gln Glu Gln Gln Gln Pro Leu Thr Leu
945                 950                 955                 960

Pro Gln Gln Gln Arg Ser Gln Gln Gln Pro Arg Cys Lys Gln Lys Val
                    965                 970                 975

Ile Phe Gly Ser Gly Thr Val Thr Phe Ser Leu Ser Phe Asp Glu Pro
                    980                 985                 990

Gln Lys Asn Ala Met Ala His Arg Asn Ser Thr His Gln Asn Ser Leu
                    995                 1000                1005

Glu Ala Gln Lys Ser Ser Asp Thr Leu Thr Arg His Gln Pro Leu
        1010                1015                1020

Leu Pro Leu Gln Cys Gly Glu Thr Asp Leu Asp Leu Thr Val Gln
        1025                1030                1035

Glu Thr Gly Leu Gln Gly Pro Val Gly Gly Asp Gln Arg Pro Glu
        1040                1045                1050

Val Glu Asp Pro Glu Glu Leu Ser Pro Ala Leu Val Val Ser Ser
        1055                1060                1065

Ser Gln Ser Phe Val Ile Ser Gly Gly Gly Ser Thr Val Thr Glu
        1070                1075                1080

Asn Val Val Asn Ser
        1085
```

METHOD AND COMPOSITIONS FOR THE IDENTIFICATION OF AGENTS THAT HAVE A POTENTIAL EFFECT AGAINST CHRONIC INFLAMMATORY DISEASES

BACKGROUND OF THE INVENTION

1. Field of the Invention

The invention concerns the fields of medicine and pharmaceutical research. Agents obtained with the invention are useful to treat chronic inflammatory conditions, in particular erosive arthritis and arteriosclerosis.

2. State of the Art

A chronic inflammatory disease is a medical condition which is characterized by persistent inflammation. Patients develop a chronic inflammatory disease because the immune system has an inappropriate response. Chronic inflammatory diseases afflict millions of people across the world leading to untold suffering, economic loss and premature death. As well as rheumatoid arthritis and osteoarthritis, these diseases include arteriosclerosis and psoriatic arthritis.

Despite the prevalence of these diseases, there have been relatively few innovative breakthroughs into revealing their cause, providing treatment or curing approaches, despite intensive global research. In particular, rheumatoid arthritis (RA) is a chronic, systemic inflammatory disease that may affect many tissues and organs, but principally attacks synovial joints. About 1% of the world's population is afflicted by rheumatoid arthritis, with women being three times more often affected than men. The current pharmaceutical treatment mainly focuses on Analgesia to suppress pain, on immunosuppressive drugs to suppress inflammation (mainly glucocorticoids and disease-modifying anti-rheumatic drugs—DMARDs) and more recently on the selective inhibition of cytokines or pathogenic cell populations like B- or T cells.

Calcium homeostasis, thus the calcium level in the peripheral blood, is regulated very narrowly and deregulation can cause serious clinical disorders, including heart failure. The cell surface calcium receptor is the primary molecular entity regulating secretion of parathyroid hormone (PTH). Activation of this receptor by extracellular calcium ions inhibits PTH secretion whereas blocking the calcium receptor stimulates secretion of PTH. Chronically elevated levels of PTH, as they occur in hyperparathyroidism, stimulate bone resorption whereas temporary increases in circulating levels of PTH stimulate bone formation. A proposed approach to treat osteoporosis is based on the use of small, orally active compounds which block the calcium receptor thereby increasing the circulating levels of endogenous PTH. Compounds acting as inhibitors of the calcium receptor are termed Calcilytics. Several patent publications propose the use of calcium receptor inhibitors for the treatment of osteoporosis, osteoarthritis and/or rheumatoid arthritis (e. g. WO2009001214, WO2008041118, U.S. Pat. No. 7,211,685 and U.S. Pat. No. 6,916,956).

Most of these calcium receptor inhibitors act on the calcium sensing receptor (CaSR) of the parathyroid gland and other tissue. As Calcilytics interfere with calcium homeostasis, their administration has to be controlled very carefully.

GPRC6A (G-protein coupled receptor family C group 6 member A) is a receptor that functions as a sensor of L-amino acids, but also binds divalent cations, including Calcium.

SUMMARY OF THE INVENTION

Objective of the Invention

The objective of the invention is to provide methods and means for the identification of agents that have a potential effect against chronic inflammatory conditions, in particular erosive arthritis and arteriosclerosis.

DESCRIPTION OF THE INVENTION

The present invention is based on two important experimental observations:

The first observation is that increased extracellular concentrations of ionized calcium are found in erosive arthritis and stimulate monocytic IL-1β release via the CaSR and GPRC6A. Simultaneous stimulation of monocytes with calcium ions and selected TLR ligands results in a 20-fold increased IL1β response compared to lipopolysaccharide (LPS) alone. During the crosstalk between GPCR and TLR signaling, phospholipase C is activated, which triggers calcium dependent potassium channels, resulting in potassium efflux, caspase-1 activation and IL-1β release. The amplification of IL1β secretion at sites of locally increased calcium ion concentrations aggravates rheumatoid arthritis.

The second important observation is that both CaSR and GPRC6A, are highly expressed in the synovial membrane of patients with rheumatoid arthritis, but expression of GPRC6A, but not of CaSR, is lower in patients with osteoarthritis (s. FIG. 1). The latter is generally not accompanied by inflammation. Thus, expression of GPRC6A appears to be upregulated in chronic inflammatory situations.

These observations indicate that GPRC6A inhibition can be a feasible therapeutic approach in inflammatory situations, in particular in chronic inflammatory diseases in which increased extracellular $Ca^{2+}$ concentrations are present, including arteriosclerosis and preferably erosive arthritis, other inflammatory arthritides and other inflammatory joint diseases.

The term erosive arthritis describes chronic inflammatory arthritides, which erode extracellular matrix and bone structure during the prolonged course of the disease. Typical examples are rheumatoid arthritis and psoriatic arthritis, and the erosive joint disease is typically accompanied by severe and long-standing inflammatory processes. The term erosive arthritis preferably further comprises other chronic inflammatory disorders that are associated with beginning bone destruction and/or increased calcium concentrations in the intermediate spaces between bones or in the joints, e. g. ankylosing spondylitis, other spondyloarthropathies. An inflammatory arthrititis that is herein not included in the term erosive arthritis, is reactive arthritis.

In contrast, osteoarthritis is typically not caused or accompanied by chronic inflammation, and was found not to be associated with increased synovial calcium concentrations. Consequently, osteoarthritis is not comprised by the terms inflammatory arthritides as used in the invention.

Based on these experimental observations the invention provides a method to identify agents that have a potential effect against chronic inflammatory conditions, in particular erosive arthritis and atherosclerosis, which are preferably specific inhibitors of GPRC6A, in particular inhibitors of GPRC6A signaling in monocytes, with the steps:

a.) providing cells expressing GPRC6A,
b.) providing cells expressing CaSR,
c.) stimulating the cells of a) and b) with extracellular calcium and/or another calcium receptor agonist, preferably aluminium, in combination with a TLR (toll-like receptor) ligand,
d.) selecting an agent that blocks the stimulation of the cells according to a.) and has no or an reduced blocking effect on the stimulation of the cells according to b.). Reduced blocking effect means that the blocking effect on the stimulation of the cells according to b.) is lower than on the cells according to a.).

The stimulation of the cells of a.) and b.) is preferably performed in parallel in separate compartments (e.g. separate wells). Alternatively, the stimulation of the cells of a.) and b.) is performed in the same compartment. In the latter case the cells of a.) and b.) are preferably marked differently (e. g. by the expression of different florescent proteins like GFP and DsRed).

The cells can be provided preferably in vitro (cell culture) or in situ (tissue culture) or alternatively in vivo in a non-human host organism (e. g. a mouse or rat). Preferably the cells (in step a. and b.) are chosen from cells selected from monocyte- or macrophage-like cells, particularly primary monocytes or macrophages, or preferably monocyte or macrophage cell lines. The cells or cell lines are most preferably derived from human or mouse origin, preferably Vitamine D3-differentiated THP-1 cells. Alternatively, the cells are murine RAW 264.7 cells.

Either GPRC6A or CaSR are expressed in monocytes preferably by stable transfection of said monocytes with genes encoding GPRC6A or CaSR. Reference sequences for human GPRC6A are listed in SEQ ID No. 10 and an encoding sequence in SEQ ID No. 9. Reference sequences for human CaSR are listed in SEQ ID No. 12 and an encoding sequence in SEQ ID No. 11. The terms GPRC6A or CaSR however comprise homologous GPRC6A sequences from other species. The terms encoding sequence encompass sequences with altered codon usage.

Cells lacking both receptors (e. g. non-differentiated THP-1 cells) and cells expressing both receptors (e. g. PMA differentiated THP-1 cells) can be used as a control.

Preferably the calcium concentration is chosen between 1.2 and 2.5 mM (mmol/L), preferably between 1.5 to 2.0 mM, most preferably 1.7 to 1.9 mM. The calcium concentration is defined herein as the concentration of free calcium ions (in the following also referred to as ionized calcium concentration or $[Ca^{2+}]$).

The TLR ligand is preferably selected from ligands of TLR1, TLR2, TLR4, TLR5, TLR6, TRL8 and TLR9, most preferably bacterial endotoxins (like lipopolysaccharides, lipoproteins and flagellin) or synthetic analogues thereof (like Pam3CSK4 and FSL-1 (Pam2CGDPKHPKSF), zymosans, heat shock proteins, unmethylated CpG Oligodeoxynucle-otide DNA and/or extracellular matrix glycoproteins, particularly tenascin, profilin, fibrinogen, heparan sulfate fragments and hyaluronic acid fragments. Particularly preferred TLR ligands are LPS and tenascin. The term lipopolysaccharide (LPS) as used herein refers to molecules comprising a lipid and a polysaccharide joined by a covalent bond found in the outer membrane of Gram-negative bacteria (like *E. Coli* and *Samonella*), and includes their isolated components (like O antigen and lipid A). The term tenascin as used herein refers to extracellular matrix glycoproteins, that are abundant in the extracellular matrix of developing vertebrate embryos and reappear around healing wounds and in the stroma of some tumors. An particular preferred tenascin is tenascin-C. Less preferred TLR ligands according to the invention are ligands of TRL3 and TRL7, in particular nucleoside derivatives (like Imiquimod (R837), an imidazoquinoline amine analogue to Guanosine), single-stranded and double-stranded RNA and poly I:C.

The TLR ligand concentration is dependent on the ligand that is used.

Preferred LPS concentrations are chosen from 10 to 1000 ng/ml, preferably 50 to 150 g/ml, most preferably 75 to 125 ng/ml. Preferred tenascin concentrations are chosen from 100 ng/ml to 100 µg/ml, preferably from 1 µg/ml to 10 µg/ml.

Other TLR ligands, like Pam3CSK4, Poly(I:C), flagellin, FSL1, Imiquimod, ssRNA, are preferably used in concentration ranges from 100 ng/ml to 100 µg/ml, more preferably from 500 ng/ml to 10 µg/ml. The concentration of unmethylated CpG Oligodeoxynucleotide DNA is preferably from 100 nM to 100 µM, more preferred from 1 µM to 10 µM.

Heat-killed or otherwise inactivated pathogens (e. g. preparation of heat-killed *Listeria* monocytogenes) are suitable TLR-ligands. Preferably, their concentration is chosen from 10 to 1000 inactivated cells/ml.

In step c.) the cells are preferably stimulated with increasing concentrations of extracellular calcium in combination with a TLR ligand, the TLR ligand preferably being LPS and/or tenascin.

The stimulation of the cells of a.) and b.) leads to activation of phospholipase C and intracellular calcium, which can both be detected as read-out. In particular for the measurement of increased intra-cellular calcium a range of established systems are available. Preferably the increased intra-cellular calcium is detected by calcium sensitive dyes (e. g. FLIPR Calcium Assay Kit, Molecular devices) or based on calcium binding fusion proteins (e. g. with GFP or Luciferase) that are introduced into the monocytes by transfection (e. g. Premo™ Cameleon Calcium Sensor, Invitrogen). Well established methods to detect increased intra-cellular calcium are summarized by Takahashi et al. 1999, Physiological Reviews, 79 (4):1089-1125) and Paredes R M 2008 Methods. 46 (3):143-51.

Advantageously, the screening method is suitable for high throughput screening. Thus, a library of pharmacological substances can be screened to identify pharmacological inhibitors of GPRC6A. In order to focus the therapeutic action on GPRC6A, which is over-expressed in the pathologic rheumatoid synovium, and to avoid side effects due to the inhibition of the more ubiquitously expressed, and less specific CaSR, the screening is focused on selective inhibitors of GPRC6A, which are tested in parallel for their lacking inhibition of the CaSR.

The term "specific inhibitors of GPRC6A" is defined herein as inhibitors that have at least a stronger antagonist effect on GPRC6A than on CaSR and preferably no effect on CaSR. The inhibitors act preferably on the GPRC6A protein on the surface of the cells or inhibit the signaling through the G-Protein or downstream signaling. However the term "inhibitors of GPRC6A" also includes agents that prevent or reduce GPRC6A activity by other means, e. g. by reducing protein stability, or by reducing protein, mRNA or gene expression.

The agents identified by the method according to the invention are preferably further tested in animal models for chronic inflammatory conditions, preferably animals (in particular mice) with collagen-induced arthritis, collagen antibody induced arthritis, Adjuvant-induced arthritis (in particular Complete Freund's adjuvant induced arthritis), urea crystal Induced arthritis, *Chlamydia* induced arthritis or carrag-eenan-induced footpad swelling.

Preferably the animal model used for this screening comprises animals, in particular mice, having aninflammatory response, which is preferably collagen or carrageenan-in-duced, that is preferably induced in the presence of a GPRC6A agonist. The GPRC6A agonist is preferably a water soluble calcium or aluminium salt.

GPRC6A deficient animals, preferably GPRC6A−/−mice, are preferably used as a control.

Another object of the invention is a kit for the identification of agents that have a potential effect against chronic inflammatory conditions, in particular erosive arthritis, which are preferably specific inhibitors of GPRC6A, in particular inhibitors of GPRC6A signaling in monocytes, comprising the following components:
 a.) cells expressing GPRC6A,
 b.) cells expressing CaSR,
 c.) at least one TLR-Ligand,
 d.) a calcium and/or another calcium receptor agonist, preferably aluminium containing buffer or stock preparation (solution or powder) thereof.

The cells and TLR-Ligand are defined and preferably selected as described above.

The invention also comprises the use of agents obtained by the method according to the invention or using the kit according to the invention in the treatment of chronic inflammatory conditions (as mentioned above), in particular erosive arthritis and arteriosclerosis.

Another object of the invention is the use of inhibitors of GPRC6A in the treatment of chronic inflammatory conditions (as mentioned above), in particular erosive arthritis and arteriosclerosis. The inhibitors of GPRC6A are preferably chosen from small hairpin RNA (shRNA) and small interference RNA (siRNA), most preferably chosen from RNA encoded by one of the following DNA sequences:

stimulated with increased Ca2+ concentration (1.7 mM) in combination with LPS for 16 hours. Transfection with siRNA (GPRC6A siRNA (h): sc-62413, SANTA CRUZ BIOTECHNOLOGY, INC., Santa Cruz, Calif. 95060 USA) inhibiting GPRC6A expression was found to significantly lower IL-1β release, while control siRNA did not. According to the manufacturer siRNA products generally consist of pools of three to five target-specific 19-25 nt siRNAs designed to knockdown gene expression. The final concentration during the 6 hour transfection was 10 nM siRNA.

FIG. 3 and FIG. 4 show that increased extra-cellular $Ca^{2+}$ concentrations occur in arthritis and stimulate monocyte IL-1β secretion:

FIG. 3a shows the calcium concentration in the medullary cavity of femoral bones from mice with collagen induced arthritis (CIA) and in control animals. FIG. 3b shows the calcium concentration in synovial fluid samples from patients with erosive rheumatoid arthritis (RA) compared to patients with other, non-destructive arthritides (control). FIGS. 3c and 3d show IL-1β release of primary CD14+ monocytes in response to increasing extracellular calcium concentration alone (c) or to increased [$Ca^{2+}$] in combination with LPS (100 ng/ml) (d) after 16 h of stimulation. The bar underneath the x axis represents the physiological range of the extracellular ionized $Ca^{2+}$ concentration (1.2 mM).

| SEQ ID | Sequence | Source (Genbank, NCBI) |
|---|---|---|
| 1 | TGCTGTTGACAGTGAGCGCGCATATTCAATCATTCTC AAATAGTGAAGCCACAGATGTATTTGAGAATGATTGA ATATGCATGCCTACTGCCTCGGA | >gnl\|Probe\|131118a.1 shRNA probe V2HS_139221 (97 bp) |
| 2 | TGCTGTTGACAGTGAGCGACCAGTGACTTCCATCAAA TTATAGTGAAGCCACAGATGTATAATTTGATGGAAGT CACTGGGTGCCTACTGCCTCGGA | >gnl\|Probe\|162364a.1 shRNA probe V2HS_235793 (97 bp) |
| 3 | TGCTGTTGACAGTGAGCGACCTTCAGCTTTGATCCCA AATTAGTGAAGCCACAGATGTAATTTGGGATCAAAGC TGAAGGCTGCCTACTGCCTCGGA | >gnl\|Probe\|162673a.1 shRNA probe V2HS_139223 (97 bp) |
| 4 | CCGGCGATCCTTATTATCTTCACTTCTCGAGAAGTGA AGATAATAAGGATCGTTTTT | >gnl\|Probe\|8651612a.1 shRNA probe TRCN\|0000008992 (57 bp) |
| 5 | CCGGCCAGGACTCATTCATAGTATTCTCGAGAATACT ATGAATGAGTCCTGGTTTTT | >gnl\|Probe\|8651613a.1 shRNA probe TRCN0000008993 (57 bp) |
| 6 | CCGGGCTGTGGAGATTATTGTCATACTCGAGTATGAC AATAATCTCCACAGCTTTTT | >gnl\|Probe\|8651614a.1 shRNA probe TRCN0000008994 (57 bp) |
| 7 | CCGGCCACAAATCCAGGAGTGTGTTCTCGAGAACACA CTCCTGGATTTGTGGTTTTT | >gnl\|Probe\|8651615a .1 shRNA probe TRCN0000008995 (57 bp) |
| 8 | CCGGGAAGCAAATAACGTGTGCATACTCGAGTATGCA CACGTTATTTGCTTCTTTTT | >gnl\|Probe\|8651616a.1 shRNA probe TRCN0000008996 (57 bp) | and complementary sequences, as well as combinations of these RNA. The sequences above are the DNA-sequences for expressing the shRNA.

BRIEF DESCRIPTION OF THE DRAWINGS

The invention is further illustrated by the following figures and examples.

Figure 3:
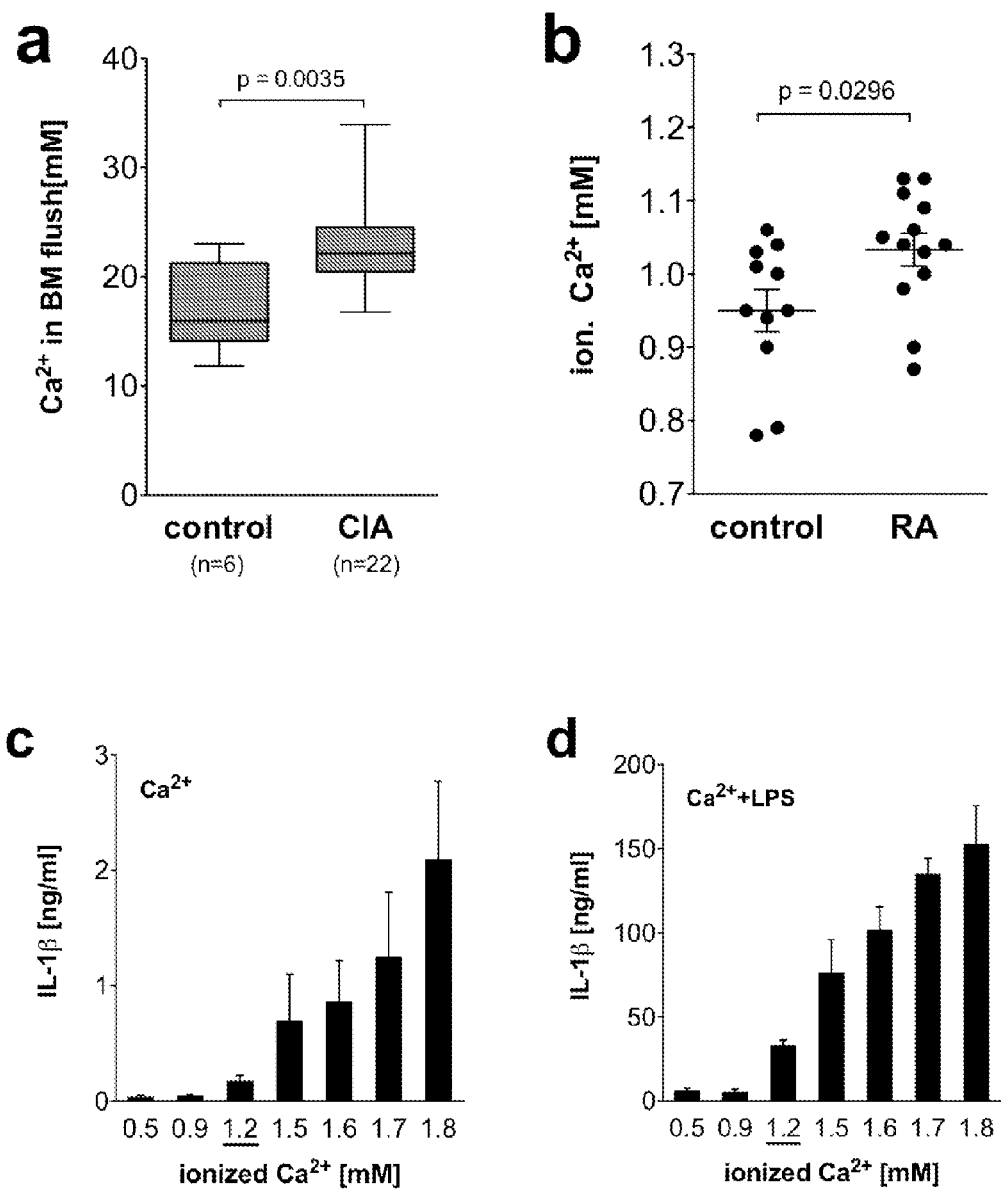
Figure 4:
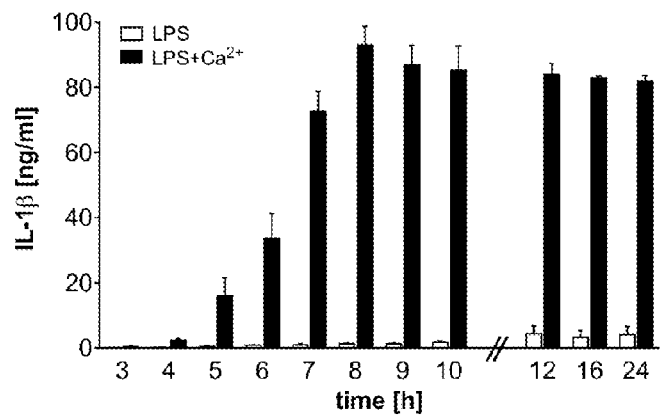
FIG. 4a shows the time course of IL-1β release of primary CD14+ monocytes after stimulation with increased extracellular calcium concentration (1.7 mM) alone (white bars) or with increased calcium concentration in combination with LPS (100 ng/ml—black bars).
FIG. 4b shows the IL-1β release of primary CD14+ monocytes in response to stimulation for 16 hours with increased extracellular calcium concentration (1.7 mM) in combination with the respective TLR stimulus as indicated. The following TLR ligands (human TLR1-9 Agonist Kit, InvivoGen) were used at the following concentrations: TLR1/2 agonist—Pam3CSK4 (1 µg/ml), TLR2 agonist—heat-killed preparation of *Listeria monocytogenes* (108 cells/ml), TLR3 agonist—Poly(I:C) (10 µg/ml), TLR4 agonist—*E. coli* K12 LPS (100 ng/ml), TLR5 agonist—*S. typhimurium* flagellin (1 μg/ml), TLR6/2 agonist—FSL1 (1 μg/ml), TLR7 agonist—Imiquimod (1 μg/ml), TLR8 agonist—ssRNA40 (1 μg/ml) and TLR9 agonist—CpG ODN2006 (5 μM). K is a control with cell culture medium.
FIG. 4c shows the IL-1β secretion of CD11b positive mononuclear cells from TLR4$^{+/+}$ and TLR4$^{-/-}$ mice in response to stimulation with either increased extracellular calcium concentration (1.7 mM), with LPS (100 ng/ml), or both.
Figure 4:
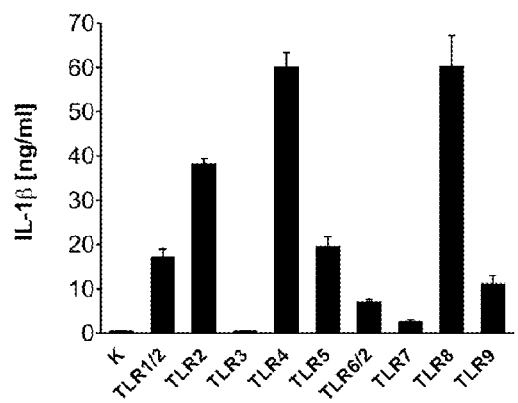
Figure 4:
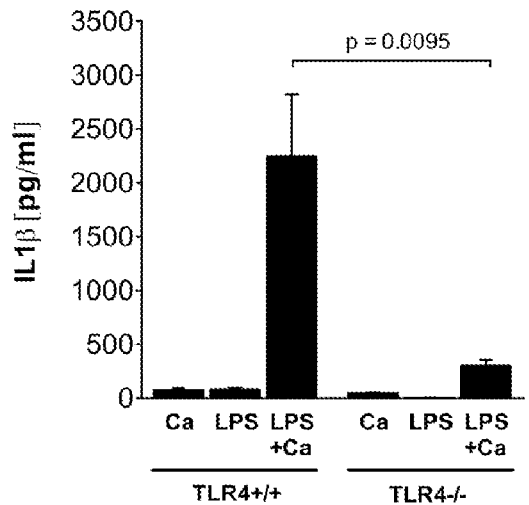

In all experiments shown in FIGS. 3 and 4, IL-1β concentrations were determined in the supernatant by ELISA.

Figure 5:
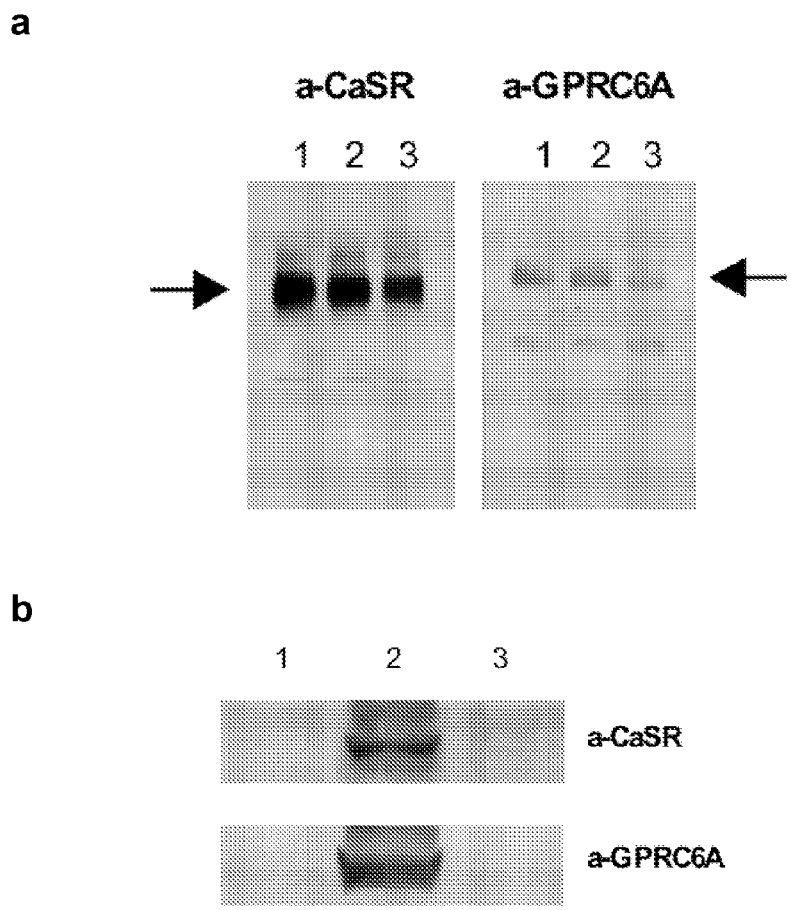

FIG. 5 demonstrates the protein expression of the two calcium receptors, CaSR (left panel) and GPRC6A (right) in primary human monocytes (FIG. 5a, in both blots lanes 1, 2 and 3 represent three different experiments from different healthy donors) and THP-1 cells (FIG. 5b, lane 2, differentiated with PMA).

Figure 6:
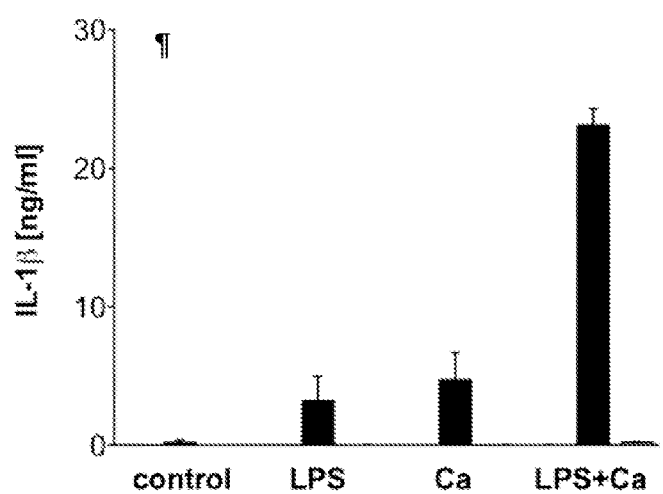
Figure 7:
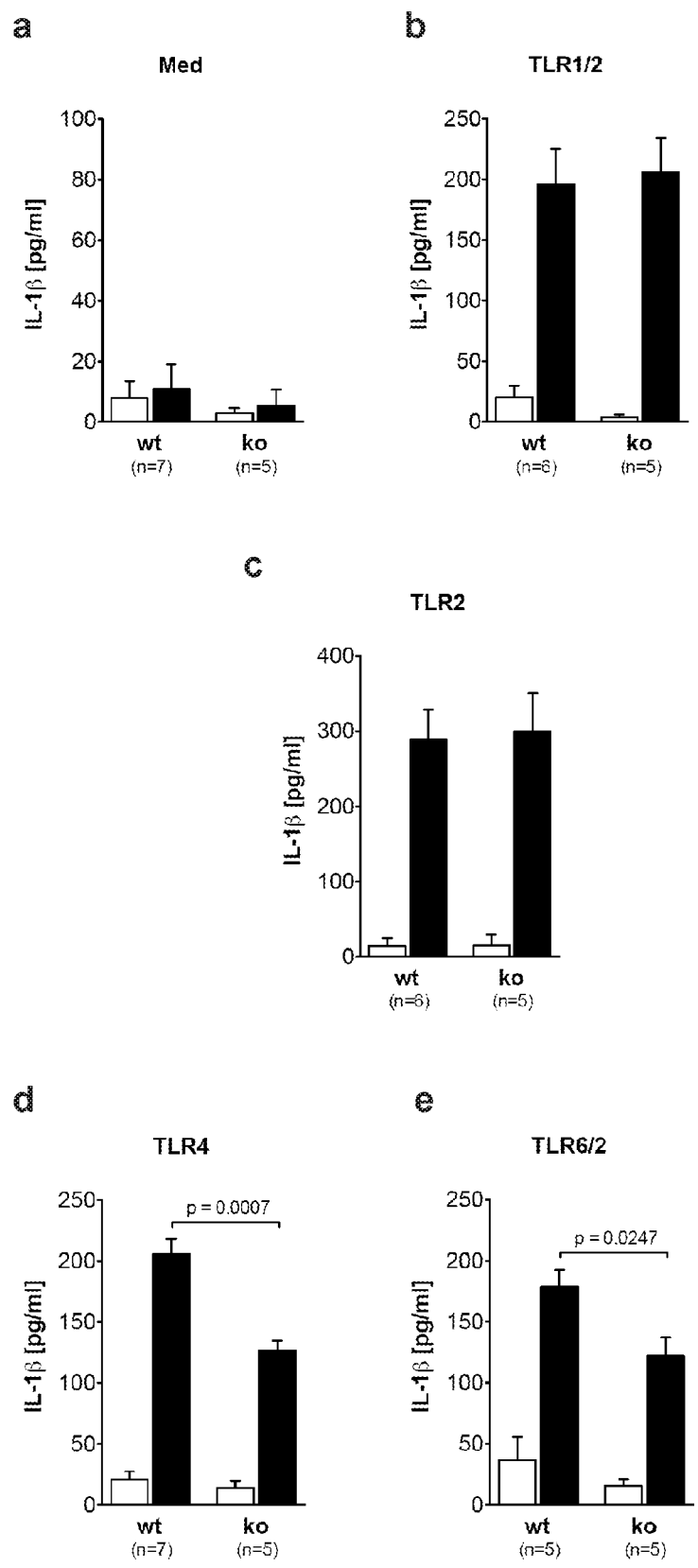

FIG. 6 shows the IL-1β release of THP-1 cells differentiated in vitro in the presence of PMA in response to stimulation for 16 hours with increased calcium concentration (1.7 mM), with LPS (100 ng/ml) or both.

FIG. 7b to FIG. 7e compare CD11b positive, monocytic cells isolated from wild type (wt) mice and GPRC6A knockout mice (ko) in their response to different TLR-ligands, white columns without Calcium, black columns with Calcium (1.7 mM)—the TLR ligands are chosen as for FIG. 4b. FIG. 7a is the medium control (med).

Figure 8:
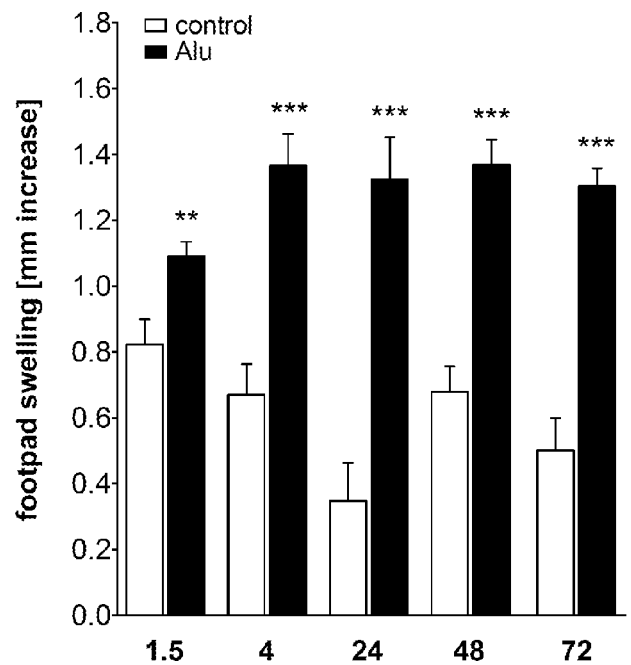

FIG. 8 illustrates the amplification of Carrageenan induced footpad swelling due to the addition of the GPRC6A agonist Aluminum (total volume of 20 μA with Aluminum Lactate 0.3 mg/100 ml and Carrageenan 1 g/100 ml) compared to the Carrageenan alone (20 μl of 1 g/100 ml) in wild type mice, ***p<0.001.

Figure 9:
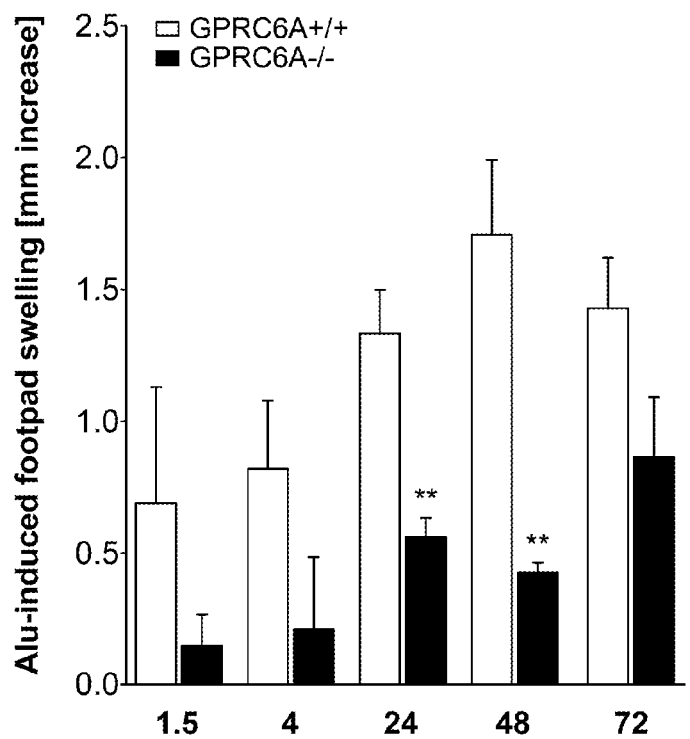

FIG. 9 illustrates the reduction of Carrageenan+Aluminum (concentrations as in FIG. 8) induced footpad swelling in GPRC6A knockout mice compared to wild type controls, indicating the profound role of the receptor in the inflammatory response, **p<0.01.

DESCRIPTION OF PREFERRED EMBODIMENTS

The results of these experiments can be summarized as follows:

The first important observation is that increased extracellular concentrations of ionized $Ca^{2+}$ are present in erosive arthritis, and are stimulatory for monocytes and macrophages. This stimulation is mediated through the G protein coupled receptors calcium sensing receptor (CaSR) and GPRC6A. Extracellular concentrations of ionized $Ca^{2+}$ in combination with a TLR (toll-like receptor) stimulus, e. g. a bacterial endotoxin like LPS (lipopolysaccharide), induce an inflammatory response, which can be characterized by measuring IL-1β (Interleukin-1beta) production, and which is increased by a factor of 20 in comparison to endotoxin (LPS) alone.

Importantly, the endogenous TLR ligands (like Tenascin), which are present in arthritis, can—in combination with increased extracellular $Ca^{2+}$ concentrations—mediate the identical effect and also elicit a dramatic increase in an inflammatory response that is comparable to the inflammatory response induced by $Ca^{2+}$ and endotoxin, and that is characterized by an IL-1β production, which is comparable to the $Ca^{2+}$ plus LPS induced levels.

If a monocytic cell line (like THP-1) is differentiated in the presence of PMA (phorbol 12-myristate 13-acetate), the resulting monocytes respond to increased $Ca^{2+}$ plus LPS concentration with similar levels of IL-1β production.

The two receptors CaSR and GPRC6A are expressed in various human cell types and tissues. CaSR expression is readily detectable in human monocytes and macrophages as well as in the synovial membrane from healthy donors and in differentiated monocytes derived from a monocytic cell line (like THP-1). GPRC6A is expressed at somewhat lower levels in human monocytes from healthy donors, but is strongly expressed in differentiated monocytes derived from a monocytic cell line (like THP-1). Expression of CaSR on a variety of cell types including monocytes has been described previously. The finding of GPRC6A expression outside of osteoblasts, bone, and calvaria, however, has not been described previously.

Expression of both receptors can readily be detected by Western blot in cellular lysates from synovial membrane biopsies from patients with rheumatoid arthritis. The CaSR is also expressed strongly in synovial membrane of patients with osteoarthritis.

Figure 1:
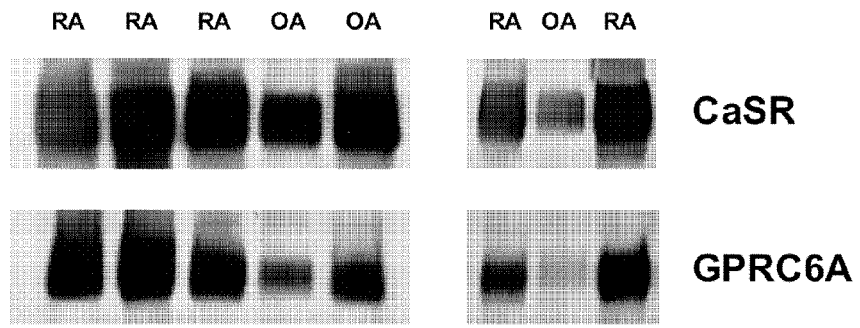
FIG. 1 shows a Western blot for the detection of calcium sensing receptor and GPRC6A in cell lysates from the synovium of patients with rheumatoid arthritis (RA) and osteoarthritis (OA).

The second important observation is that for GPRC6A, in contrast, a high expression was found in the synovial membrane of patients with rheumatoid arthritis, while its expression was lower in patients with osteoarthritis (FIG. 1), which is not caused by inflammation. Thus, expression of GPRC6A seams to be higher in inflammatory situations.

Figure 2:
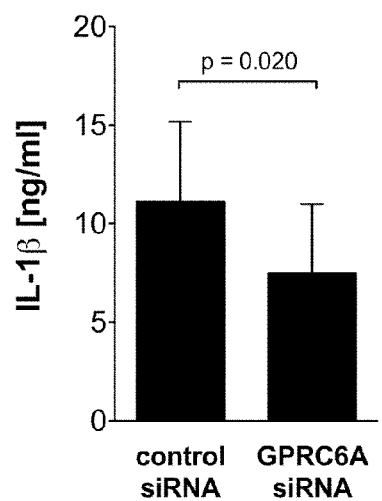
FIG. 2 shows IL-1β secretion of THP-1 cells, that were differentiated in the presence of PMA and subsequently

When the expression of GPRC6A was down-regulated in differentiated monocytes, the IL-1B secretion induced by stimulation with $Ca^{2+}$ in combination with LPS was inhibited significantly (FIG. 2).

The $Ca^{2+}$ plus LPS-induced effect was nearly abrogated in TLR4-deficient C3H/HeJ mice indicating that the stimulatory LPS effect was indeed due to TLR signaling induced by TLR4 stimulation with LPS (FIG. 4c).

The experiments comparing the GPRC6A knockout mice to the wild type indicate the profund role of GPRC6A in the inflammatory response.

Antibodies and Reagents

Rabbit-polyclonal anti-CaSR and anti-GPRC 6A Abs and peroxidase-conjugated goat-anti-rabbit secondary Ab were obtained from Santa Cruz Biotechnology. Flow cytometry anti-CD14 were from Miltenyi Biotec. Tenascin-C from Millipore, anti-IL-1β Ab and isotype control from R&D Systems.

Cytokine Measurement

Human and murine IL-1β were measured by commercially available enzyme-immunoassay following the manufacturer's protocol.

Human Subjects

Control subjects were recruited among healthy blood donors. Synovial biopsy specimens were obtained from 5 patients with rheumatoid arthritis (RA) and 3 with osteoarthritis who underwent synvectomy in the Department of Orthopedics at Leipzig University. Synovial fluid was obtained from 14 RA patients and 11 patients with other non-destructive arthritides (6× reactive arthritis, 5× osteoarthritis) by aspiration for therapeutic purpose. All experiments with human materials were approved by the local ethics committee and informed consent was obtained from all subjects.

Animal Experiments

Collagen induced arthritis (CIA) in DBA/1J-mice (Harlan-Winkelmann, Borchen, Germany) was induced and the clinical severity quantified as described previously (Pierer et al. 2009. J Immunol 182, 3139-3145).

For the TLR4$^{-/-}$ experiments, homozygous C3H/HeJ mice which carry a point mutation in the Tlr4-gene10 were used. The C57BL/10ScSnJ is the progenitor strain from which the TLR4-mutant strain is derived and was used as control (all from The Jackson Laboratory, Bar Harbor, Me., USA).

Mice were bred and maintained at the animal facilities at the Medizinisch-Experimentelles-Zentrum, University of Leipzig, Germany. All experiments were approved and performed according to institutional guidelines of the animal ethics committee at the University of Leipzig.

Cell Isolation

Human monocytes were isolated as described previously (Rossol et al. 2005. Arthritis Res Ther 7, R1189-R1199; Rossol et al. 2007 J Immunol 179, 4239-4248).

Mice bone marrow was obtained by aspirating the femurs. Peripheral blood was harvested by heart puncture. CD11b$^+$ monocytes were isolated from mononuclear cells by positive magnetic separation (Miltenyi Biotech). Peritoneal macrophages were recovered by peritoneal lavage with 5 ml cold PBS and used without further separation.

Cell Culture and Calcium Titration

Monocytes (3×105/200 µl) were incubated in RPMI1640 supplemented with 10% heat-inactivated FCS, 2 mM L-glutamine, 100 U/ml penicillin, 100 µg/ml streptomycin. The monocytic cell line THP-1 (DMSZ) was differentiated for two days with 100 ng/ml PMA or 100 nM vitamin D3.

LPS (*Escherichia coli* 0111:B4 ultrapure, 100 ng/ml, Invivogen) was used at a concentration of 100 ng/ml. To incubate monocytes in media containing increasing ionized calcium concentration, $CaCl_2$ was added to the culture. Final $Ca^{2+}$ ion concentrations in the media were measured after anaerobic sampling (sealed blood gas syringes were completely filled under an $CO_2$ atmosphere, and were closed with caps to avoid loss of $CO_2$) on an ABL 730 (Radiometer). The amount of $CaCl_2$ added into the culture medium and the resulting ionized calcium concentration are indicated in Tab. 1.

TABLE 1

Titration of Ca2+ ion concentrations in the culture media

| Added $CaCl_2$ | Measured ionized $Ca_2+$ |
|---|---|
| 0 | 0.6 mM |
| 0.5 mM | 0.9 mM |
| 1.0 mM | 1.2 mM |
| 1.5 mM | 1.5 mM |
| 2.0 mM | 1.6 mM |
| 2.5 mM | 1.7 mM |
| 3.0 mM | 1.8 mM |

A final ionized calcium concentration of 1.7 mM was used in the experiments, which was achieved by adding 2.5 mM $CaCl_2$ to the culture medium.

Measurement of Calcium Concentration

Synovial fluid was obtained by anaerobic sampling and the $Ca^{2+}$ concentration was measured on an ABL 730 (Radiometer GmbH). To determine the $Ca^{2+}$ concentration in bone marrow of mice, bone marrow was obtained by flushing the femur once with 100 µl 0.9% NaCl. Cells were removed by centrifugation. The $Ca^{2+}$ concentration was measured in the supernatant. The final $Ca^{2+}$ ion concentration was calculated by multiplying the measured $Ca^{2+}$ concentration in 100 µl with the dilution factor (ratio of the 100 µl flush volume and the estimated volume of the flushed bone marrow cavity of the femur).

Cell Lysis, Gel Electrophoresis and Western Blotting

The expression of CaSR and GPRC6A was analyzed by western blotting. 3×10$^6$ cells were lysed with Radioimmunoprecipitation assay buffer (RIPA-buffer). Synovial tissue was cut into small pieces, and 100 mm$^3$ tissue was lysed with 100 µl RIPA-buffer. Protein concentrations were determined with a detergent-compatible-protein-assay (Biorad). Aliquots of the supernatants were incubated in non-reducing Laemmli-buffer for 30 min at 20° C. (CaSR/GPRC6A) and equal amounts of protein were resolved by SDS-PAGE. Gel electrophoresis and western blotting was performed as described previously (Rossol et al. 2007. J Immunol 179, 4239-4248).

Statistical Analysis

For statistical analysis the software Sigma Stat was used. Prior to all comparisons, a normality test was performed. To assess statistical significance, students t-Test or Mann Whitney Rank Sum test was used.

Screening Method

The screening of a chemical library is performed in order to obtain agents that have a potential effect against chronic inflammatory conditions, in particular erosive arthritis and arteriosclerosis, as follows:

Firstly, undifferentiated THP-1 cells are transduced with the genes encoding human GPRC6A (SEQ ID No. 9 and 10, NCBI Reference Sequence: NM_148963.2, cells of type a.)) and human CaSR (SEQ ID No. 11 and 12, Genbank: U20760.1, cells of type b.)) by using retroviral vectors as described in Rossol et al. 2007 (J Immunol 179, 4239-4248).

The following vectors were used:

GPRC6A full length in pCMV6-AC-Neo Vektor (Origene, Rockville, Md., USA),

CaSR full length in pCMV6-XL4 Vektor (Origene).

The cells are seeded separately into 384-well plates (10,000 cells/well). The cells are cultured as described above, stimulated by adding 100 ng/ml LPS plus either 1.7 mM calcium or 1 µl Tenascin-C to the culture medium and incubated for 16 h. The substances of the chemical library are added to the wells with type a.) and b.). The following controls were used: without stimulus (no added Calcium, no LPS no Tenascin-C), with LPS without Calcium, with Calcium without, and without added substances of the chemical library.

The stimulation of the cells leads to increase of intracellular calcium that is detected with the FLIPR Calcium Assay Kit (Molecular devices, Sunnyvale, Calif. USA) according to the manufactures protocol and a fluorescence plate reader (488 nm Excitation, 510-570 nm emission). Wells with cells of type a.) and b.) and the same stimulus and library substances are compared. Library substances that show no or low intracellular calcium in the wells with cells of type a.) and increased intracellular calcium in the wells with cells of type b.) are selected for further testing in the mouse CIA model.

Animal Model

A mouse strain on b16 background, in which GPRC6A has been knocked out, and which is characterized only by a mild metabolic phenotype (Wellendorph P, Johansen L D, Jensen A A, Casanova E, Gassmann M, Deprez P, ClŽment-Lacroix P, Bettler B, BrŠuner-Osborne H.: J Mol Endocrinol. 2009 March; 42 (3):215-23.) was investigated to the relevance of GPRC6A (and of its knockout) for $[Ca^{2+}]_o$ plus LPS-induced IL-1β release in in vitro experiments.

The experiments were performed with CD11b positive, monocytic cells isolated from the murine bone marrow obtained by flushing the femural bone as described above. Cells were stimulated in vitro with the same calcium and TLR ligand concentration described above.

The results in FIG. 7A to FIG. 7E show that GPRC6A knockout cells produce significantly less IL-1 beta upon stimulation with $[Ca^{2+}]_o$ plus LPS (labelled as TLR4) and upon stimulation with [Ca2+]o plus a TLR2/6 ligand.

To test the clinical efficacy of the identified inhibitors of GPRC6A an animal model of the inflammatory response was developed in wild type b16 mice and using GPRC6A knock out mice as a control. For that purpose, a local inflammation was induced by injection of Carrageenan (20 microliter, 1 g/100 ml) combined with 0.3 mg Aluminum Lactate dissolved in 0.1M sodium acetate into the footpads of the hind leg, and footpad swelling was measured.

FIG. 8 illustrates the amplification of Carrageenan induced footpad swelling due to the addition of Aluminum compared to the Carrageenan alone in wild type mice. In FIG. 9 the reduction of Carrageenan+Aluminum induced footpad swelling in GPRC6A knockout mice compared to wild type controls is illustrated, indicating the profound role of the receptor in the inflammatory response.

What is claimed is:

1. Method for the identification of agents that have a potential effect against chronic inflammatory conditions, comprising:
   a.) providing cells expressing GPRC6A,
   b.) providing cells expressing CaSR,
   c.) stimulating the cells according to a.) and b.) with at least one TLR-ligand and calcium and/or another calcium receptor agonist,
   d.) selecting an agent that blocks the stimulation of the cells according to a) and has no or a reduced blocking effect on the stimulation of the cells according to b.).

2. Method according to claim 1, wherein the cells are chosen from monocyte cell lines.

3. Method according to claim 1, wherein the agents identified are further tested in an animal model for chronic inflammatory conditions.

4. Method according to claim 1, wherein the calcium receptor agonist is aluminium.

* * * * *